United States Patent
Bureau

(10) Patent No.: US 9,844,631 B2
(45) Date of Patent: Dec. 19, 2017

(54) INJECTION DEVICE HAVING A MINIATURIZED DRUG DELIVERY PORTION

(71) Applicant: Becton Dickinson France, Le Pont de Claix (FR)

(72) Inventor: Christophe Bureau, Saint-Martin d'Uriage (FR)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 14/384,252

(22) PCT Filed: Mar. 13, 2013

(86) PCT No.: PCT/IB2013/000742
§ 371 (c)(1),
(2) Date: Sep. 10, 2014

(87) PCT Pub. No.: WO2013/136176
PCT Pub. Date: Sep. 19, 2013

(65) Prior Publication Data
US 2015/0057611 A1 Feb. 26, 2015

Related U.S. Application Data

(60) Provisional application No. 61/610,184, filed on Mar. 13, 2012, provisional application No. 61/610,189, (Continued)

(51) Int. Cl.
*A61M 5/31* (2006.01)
*A61M 37/00* (2006.01)
(Continued)

(52) U.S. Cl.
CPC .......... *A61M 5/3129* (2013.01); *A61M 5/145* (2013.01); *A61M 5/155* (2013.01);
(Continued)

(58) Field of Classification Search
CPC .... A61M 5/145; A61M 5/00; A61M 37/0015; A61M 2037/0023; B65B 3/10; A61B 17/205
See application file for complete search history.

(56) References Cited

U.S. PATENT DOCUMENTS

| | | | |
|---|---|---|---|
| 5,370,635 A | 12/1994 | Strausak et al. | |
| 5,900,238 A | 5/1999 | Gombotz et al. | |
| | (Continued) | | |

FOREIGN PATENT DOCUMENTS

| | | |
|---|---|---|
| EP | 1852142 A1 | 11/2007 |
| JP | 2005525141 A | 8/2005 |
| | (Continued) | |

OTHER PUBLICATIONS

Song et al., Microneedle Delivery of H5N1 Influenza Virus-Like Particles to

Related U.S. Application Data filed on Mar. 13, 2012, provisional application No. 61/661,032, filed on Jun. 18, 2012, provisional application No. 61/661,020, filed on Jun. 18, 2012, provisional application No. 61/669,846, filed on Jul. 10, 2012.

(51) Int. Cl.
| | |
|---|---|
| *A61M 5/155* | (2006.01) |
| *B65B 3/10* | (2006.01) |
| *A61M 5/50* | (2006.01) |
| A61M 5/24 | (2006.01) |
| A61M 5/145 | (2006.01) |
| A61M 5/142 | (2006.01) |

(52) U.S. Cl.
CPC ...... *A61M 5/5086* (2013.01); *A61M 37/0015* (2013.01); *B65B 3/10* (2013.01); *A61M 5/14244* (2013.01); *A61M 5/2425* (2013.01); *A61M 2005/14513* (2013.01); *A61M 2005/314* (2013.01); *A61M 2037/0023* (2013.01); *A61M 2037/0053* (2013.01); *A61M 2205/33* (2013.01); *A61M 2205/59* (2013.01)

(56) References Cited

U.S. PATENT DOCUMENTS

| | | | |
|---|---|---|---|
| 5,942,242 A | 8/1999 | Mizushima et al. | |
| 6,045,534 A | 4/2000 | Jacobsen et al. | |
| 6,086,562 A | 7/2000 | Jacobsen et al. | |
| 6,099,853 A | 8/2000 | Hertelendy et al. | |
| 6,322,539 B1 * | 11/2001 | Cook | A61M 25/02 604/174 |
| 6,485,462 B1 * | 11/2002 | Kriesel | A61M 5/14276 604/132 |
| 6,494,865 B1 | 12/2002 | Alchas | |
| 6,565,532 B1 | 5/2003 | Yuzhakov et al. | |
| 6,569,143 B2 | 5/2003 | Alchas et al. | |
| 6,656,147 B1 | 12/2003 | Gertsek et al. | |
| 6,800,070 B2 | 10/2004 | Mazidji et al. | |
| 6,896,666 B2 | 5/2005 | Kochamba | |
| 6,929,950 B2 | 8/2005 | Canham et al. | |
| 6,953,455 B2 | 10/2005 | Cho et al. | |
| 6,958,691 B1 | 10/2005 | Anderson et al. | |
| 6,991,779 B2 | 1/2006 | Steiner et al. | |
| 7,135,191 B2 | 11/2006 | Hertelendy et al. | |
| 7,225,807 B2 | 6/2007 | Papania et al. | |
| 7,429,258 B2 | 9/2008 | Angel et al. | |
| 7,670,314 B2 | 3/2010 | Wall et al. | |
| 7,758,855 B2 | 7/2010 | Kopecko et al. | |
| 7,867,405 B2 | 1/2011 | Spitz et al. | |
| 7,896,841 B2 | 3/2011 | Wall et al. | |
| 7,998,119 B2 | 8/2011 | Yeshurun et al. | |
| 8,007,466 B2 | 8/2011 | Yeshurun et al. | |
| 8,684,968 B2 | 4/2014 | Genosar | |
| 2002/0009463 A1 | 1/2002 | Raa et al. | |
| 2003/0045492 A1 | 3/2003 | Tang et al. | |
| 2003/0104010 A1 | 6/2003 | Raa et al. | |
| 2003/0153900 A1 * | 8/2003 | Aceti | A61B 5/1411 604/890.1 |
| 2003/0190332 A1 | 10/2003 | Gilad et al. | |
| 2004/0092875 A1 | 5/2004 | Kochamba | |
| 2004/0134495 A1 | 7/2004 | Eigemann et al. | |
| 2005/0165380 A1 | 7/2005 | Kochamba | |
| 2005/0209566 A1 | 9/2005 | Yeshurun et al. | |
| 2006/0015061 A1 | 1/2006 | Kuo et al. | |
| 2006/0239931 A1 | 10/2006 | Eyles et al. | |
| 2006/0264926 A1 | 11/2006 | Kochamba | |
| 2007/0010810 A1 | 1/2007 | Kochamba | |
| 2007/0060837 A1 | 3/2007 | Cho et al. | |
| 2007/0078376 A1 * | 4/2007 | Smith | A61M 37/0015 604/21 |
| 2007/0088248 A1 | 4/2007 | Glenn et al. | |
| 2007/0276320 A1 | 11/2007 | Wall et al. | |
| 2007/0293826 A1 | 12/2007 | Wall et al. | |
| 2008/0131377 A1 | 6/2008 | Eyles et al. | |
| 2009/0012494 A1 | 1/2009 | Yeshurun et al. | |
| 2009/0054842 A1 | 2/2009 | Yeshurun et al. | |
| 2009/0069788 A1 | 3/2009 | Yeshurun et al. | |
| 2009/0163868 A1 | 6/2009 | Hoel et al. | |
| 2009/0182306 A1 | 7/2009 | Lee et al. | |
| 2010/0111984 A1 | 5/2010 | D'Souza | |
| 2010/0185177 A1 | 7/2010 | Gillum | |
| 2010/0211005 A1 | 8/2010 | Edwards et al. | |
| 2011/0040245 A1 | 2/2011 | Garcia De Castro Andrews | |
| 2011/0059150 A1 | 3/2011 | Kendall et al. | |
| 2011/0172639 A1 | 7/2011 | Moga et al. | |
| 2011/0238038 A1 | 9/2011 | Sefi et al. | |
| 2011/0282298 A1 | 11/2011 | Agian et al. | |
| 2012/0323183 A1 | 12/2012 | Peterson et al. | |

FOREIGN PATENT DOCUMENTS

| | | |
|---|---|---|
| JP | 2006500086 A | 1/2006 |
| JP | 2009513365 A | 4/2009 |
| WO | 02083213 A1 | 10/2002 |
| WO | 2006031856 A2 | 3/2006 |
| WO | 2008083209 A2 | 7/2008 |
| WO | 2009023549 A2 | 2/2009 |
| WO | 2010007565 A2 | 1/2010 |
| WO | 2010067319 A2 | 6/2010 |
| WO | 2011042542 A1 | 4/2011 |

* cited by examiner

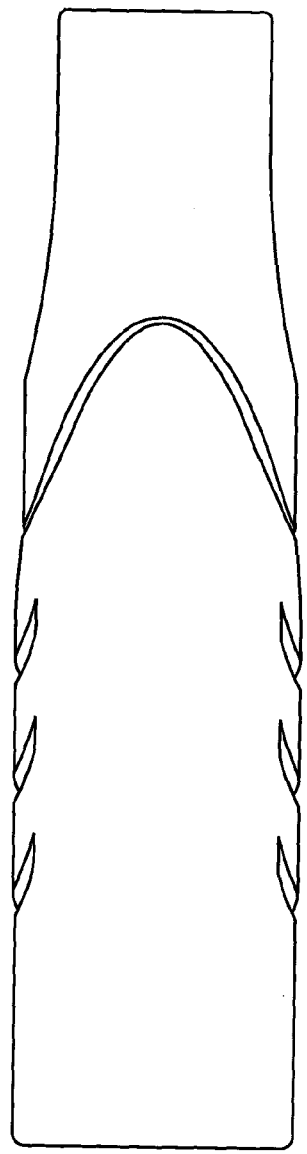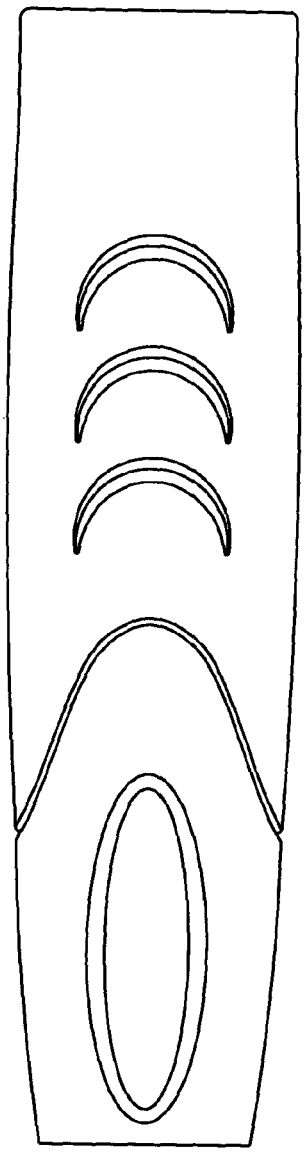
FIG.13A PRIOR ART
FIG.13B PRIOR ART

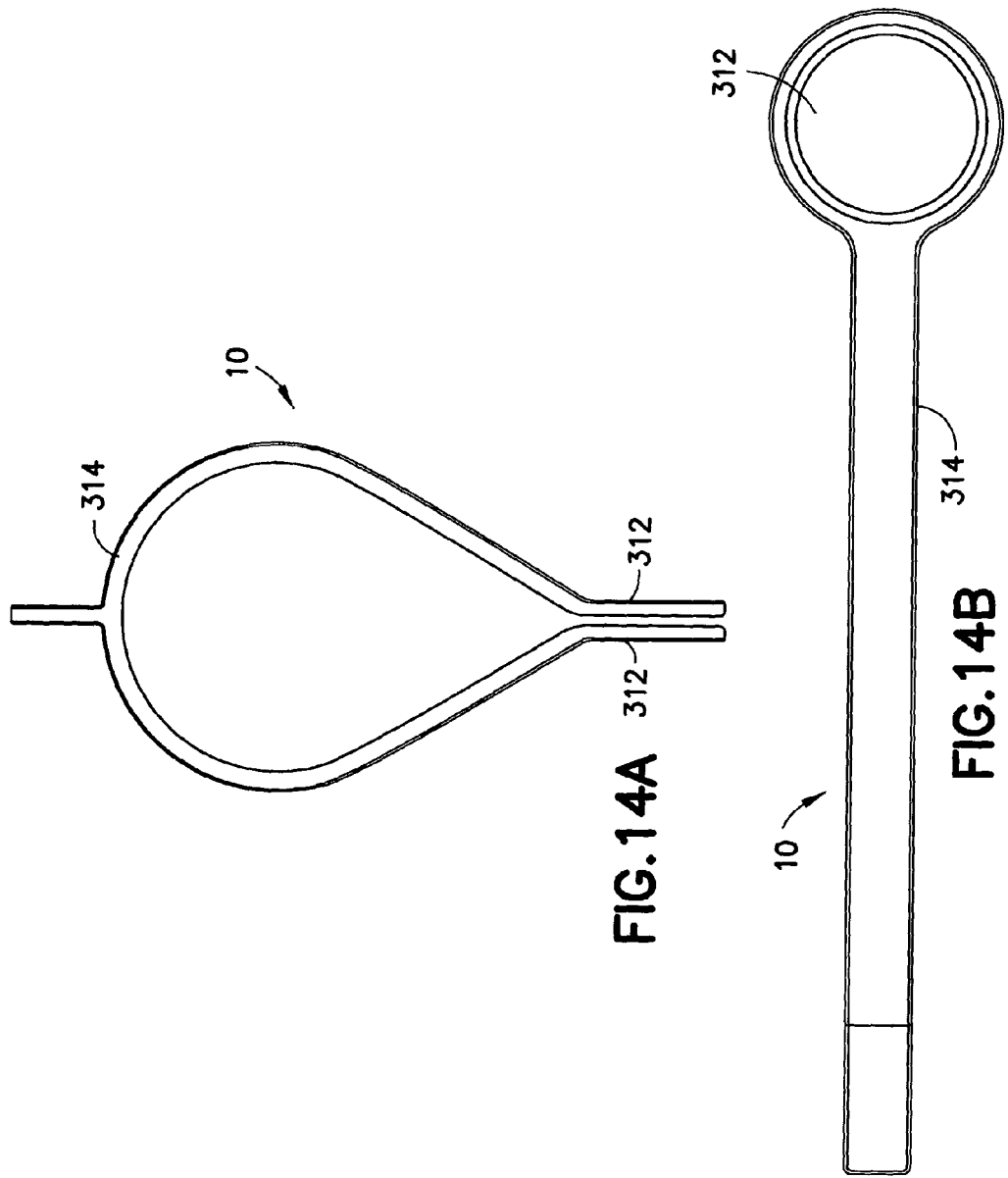

INJECTION DEVICE HAVING A MINIATURIZED DRUG DELIVERY PORTION

CROSS-REFERENCE TO RELATED APPLICATIONS

This application is the United States national phase of International Application No. PCT/IB2013/000742 filed Mar. 13, 2013, and claims priority to U.S. Provisional Patent Application Nos. 61/610,184 and 61/610,189, both filed Mar. 13, 2012; 61/661,032 and 61/661,020, both filed Jun. 18, 2012; and 61/669,846 filed Jul. 10, 2012, the disclosures of which are hereby incorporated in their entirety by reference.

BACKGROUND OF THE INVENTION

Field of the Invention

The present invention relates generally to an injection device, and, more specifically, to an injection device with a miniaturized drug delivery portion.

Description of Related Art

Current vaccination programs have numerous financial and logistical problems. In emerging countries, public health officials have, so far, been largely unsuccessful in carrying out large scale vaccination initiatives. One reason for the lack of success stems from the logistical difficulties in transporting large populations to a limited number of distant immunization clinics where professionals have sufficient expertise to perform the inoculation. While charitable organizations and non-governmental organizations provide considerable amounts of money to cover vaccine costs, the lack of infrastructure has prevented these vaccines from reaching many rural populations.

In developed countries, doctor shortages are increasing and long standing policy issues have made the distribution of vaccines complex. In times of increased need for vaccines, vaccine distribution is often managed "on-the-fly". As the average population in these developed countries continues to increase, the need for vaccinations in response to flu outbreak will certainly increase. Further, the existing immunization infrastructures are insufficient for responding to pandemic situations. World health experts continue to caution that as global integration increases, the possibility of a rapidly spreading world-wide flu pandemic continues to increase.

The problems associated with providing immunization on a large scale generally result from a combination of (1) how vaccinations are administered and (2) currently available injection devices. Receiving a vaccine or drug through injection most typically requires at least one appointment with a medical provider such as a General Practitioner (GP). The injection is generally performed by a trained professional such as a nurse. In many countries, the cost of a GP appointment, not including the cost of the drug or injection itself, is significant. Further, many countries are currently experiencing a shortage of GPs and other trained medical professionals. This shortage could be alleviated in part if medical professionals spent less time performing trivial procedures, such as injections, and more time diagnosing and treating more complex medical conditions. It is evident that a significant saving in time and expense could be realized if untrained individuals could perform injections of vaccines and other therapeutic agents on themselves.

It is further understood, that a general trend in healthcare is that the cost-per-capita must decrease. Notably, as populations age and as countries have less money to spend on healthcare costs, the amount of money available for healthcare expenditures per person will necessarily decrease. Consequently, patients will perform greater numbers of treatments by themselves to eliminate the cost associated with visiting a healthcare professional for simple (e.g., non-diagnostic) procedures. This is already occurring for patients affected by diabetes, rheumatoid arthritis, or multiple sclerosis and could become the standard for other treatments including contraceptives, cosmetics, or vaccines in the future. Individuals who perform treatments on themselves have different needs and requirements than patients receiving treatment from a trained professional. Accordingly, the types of medication dispensing apparatus attractive to untrained individuals will be different than the types of apparatus used by trained medical professionals.

A wide variety of hypodermic injection devices for fluid injections are currently commercially available. Most hypodermic injections are intended to be intramuscular, requiring that a hypodermic needle penetrates through an individual's skin layer and subcutaneous tissue and into the muscle. Needles of this type generally cause pain, damage to the skin at the site of insertion, and bleeding, which increases the risk of disease transmission and infection at the wound site. Intramuscular injections also generally require administration by one trained in needle use. Problems of pain, wound formation, and the general skill required to perform the injection mean that intramuscular injections are difficult to perform outside of a medical facility and especially difficult for untrained individuals to perform self-injections.

An alternative delivery technique is the transdermal patch, which relies on diffusion of a drug across the skin. However, transdermal delivery devices are not useful for many drugs, due to the poor permeability (i.e., effective barrier properties) of the skin. The rate of diffusion depends in part on the size and hydrophilicity of the drug molecules and the concentration gradient across skin layers. In fact, few drugs have the necessary properties to be effectively delivered through the skin by passive diffusion. While providing varying degrees of enhancement can increase permeability for some substances, these techniques are not suitable for all types of drugs. In some cases, transdermal drug delivery is also painful and inconvenient for users. Last but not least, clinical trials of diarrhea, flu, and measles vaccines have all failed to reach therapeutically effective levels when delivered intradermally.

A second alternative drug delivery possibility is a mini-needle syringe. Mini-needle syringes allow for intradermal injection of a drug at clinically relevant rates through one or more layers of skin with minimal damage, pain, or irritation to the surrounding tissue. Mini-needle syringes include a needle shaft having a cross-sectional dimension of between about 1 µm and 500 µm. In many cases, the puncture site formed by a mini-needle is less than about 0.2 µm in diameter. The small diameter of the puncture site reduces pain and increases healing time, significantly reducing the possibility of infection. An example of such an intradermal delivery device and needle assembly is disclosed in U.S. Pat. No. 6,494,865 assigned to Becton, Dickinson and Company and incorporated herein by reference. However, it is recognized that while mini-needle syringes effectively reduce pain, many individuals are, nevertheless, intimidated by the prospect of performing an injection on themselves. Thus, it can be concluded that it is the fear and anticipation of the injection process, rather than the pain itself, that prevents many individuals from performing injections on themselves.

More recently still, miniaturized drug delivery devices based on patch-like designs have been envisioned which further miniaturize the needle assembly. These devices are manufactured using micro-scale manufacturing techniques developed for the semiconductor industry and are suitable for mass production. Typically, such devices involve microneedles produced from a substrate such as a silicon base by, for example, press extrusion techniques in which force exerted on a top portion of the substrate produces a pointed tip extending from the base of the substrate. Often the tip portions of the microneedles are shaped and dimensioned to carry a biologically active substance. The plurality of needles pierces and penetrates into target cells within tissue, so that the biological substance is transferred from the tip portion and deposited within the target cells.

However, such tip loading is not effective to deliver a precisely metered dose of a biologically active substance. Generally, medical treatment methodologies that include injection into a patient require precisely controlling the amount of drug delivered which cannot be accomplished with tip coating. Further, microneedles produced by this process pierce the stratum corteum of the skin, but do not extend into the dermis. Accordingly, such microneedles are generally unable to facilitate delivery of drugs which cannot diffuse through the dermis layer of skin. Vaccines are an example of a therapeutic agent that cannot diffuse through the epidermis or stratum corteum.

Therefore, it is desirable to provide an injection device and method of manufacture thereof for the injection of a therapeutic or preventative agent having a miniaturized drug delivery portion and non-functional elements designed to increase a user's willingness to use the device. It is also desirable to provide an injection device that a user can confidently and easily use without requiring special instructions or training to perform the injection.

SUMMARY OF THE INVENTION

An embodiment of the present invention is directed to an injection device configured with a structure and shape to be attractive to a user and which instills confidence in a user that the device will operate accurately and effectively while an injection is performed. More preferably still, the device should not have the appearance or functionality of a traditional syringe to reduce the user's fear and anticipation associated with the standard injection process. Ideally, users should not be reminded of traditional syringe injections when performing the self-injection. More preferably still, the device should permit relatively rapid delivery of a single dose of a therapeutic agent. Users will want the injection process to be completed quickly to avoid increased anticipation or fear.

Provided herein is a self-injection device having a miniaturized drug delivery portion which includes a housing and a drug delivery portion enclosed within the housing. The device is intended to be engagable with a user through the skin of the user. The drug delivery portion includes a reservoir containing a fluid to be delivered to a user, and a needle in fluid communication with the reservoir and extendable through at least a portion of the housing. The drug delivery portion further includes a drive mechanism for expelling fluid from the reservoir through the needle. An $R^1$ value defining the ratio between the aspect ratio (AR) of the housing of the device and the aspect ratio (AR) of the functional portion of the self-injection device is at least 100%.

In accordance with an embodiment of the present invention, a self-injection device with a miniaturized drug delivery portion includes a housing having an interior volume and a drug delivery portion having a volume enclosed within the housing. The drug delivery portion includes a reservoir containing a fluid to be delivered to a user, and a microneedle in fluid communication with the reservoir and extendable through the housing. The drug delivery portion also includes a drive mechanism for expelling fluid from the reservoir through the microneedle, wherein the volume of the drug delivery portion is less than 40% of the interior volume of the housing.

In certain embodiments, the volume of the drug delivery portion is less than 30% of the interior volume of the housing. In other embodiments, the volume of the drug delivery portion is less than 20% of the interior volume of the housing. The microneedle may be configured for intradermal injection. The microneedle may be extendable from the housing a distance of between 1 mm and 2 mm.

In certain configurations, the reservoir contains a single dose of at least one of a vaccine, a medicament, and a therapeutic agent. The drive mechanism may expel fluid from the reservoir as a single continuous dose delivered at a clinically reasonable rate. The clinically reasonable rate may be a total delivery time of no longer than 10 seconds. The self-injection device may include an activator for engaging the drive mechanism. Once engaged by the activator, the drive mechanism may passively expel fluid from the reservoir. The self-injection device may also include a wireless receiver associated with the drive mechanism. In that case, the activator is configured to engage the drive mechanism when an activation instruction is received by the wireless receiver from an external control device. The self-injection device may further include an indicator which alerts a user when the fluid has been substantially expelled from the reservoir. Optionally, the self-injection device further includes a wireless transmitter, which is configured to transmit an alert to an external control device when the fluid has been substantially expelled from the reservoir.

In certain configurations, the driver mechanism of the self-injection device is a plurality of expandable members connected to the reservoir. When activated, the expandable members expand to expel fluid from the reservoir. The expandable members may include hydrophilic ionic particles, which expand when exposed to water, or heat activated expandable cells.

In accordance with another embodiment of the present invention, a self-injection device with a miniaturized drug delivery portion includes a housing having an interior volume and a drug delivery portion having a volume enclosed within the housing. The drug delivery portion includes a reservoir containing a fluid to be delivered to a user, and a microneedle in fluid communication with the reservoir and extendable through the housing. The drug delivery portion also includes a drive mechanism for expelling fluid from the reservoir through the microneedle, wherein an aspect ratio of the drug delivery portion:the interior volume of the housing defined by the equation $$AR = \frac{L3}{\sqrt{L1^2 + L2^2}}$$

is greater than 100%.

In certain configurations, a dimension of the drug delivery portion divided by the corresponding length of the housing is less than 40%. In other configurations, a dimension of the drug delivery portion divided by the corresponding length of the housing is less than 30%. In still other configurations, a dimension of the drug delivery portion divided by the corresponding length of the housing is less than 25%.

The fluid-containing reservoir may contain a single dose of a therapeutic agent. The drive mechanism may expel fluid from the reservoir as a single continuous dose delivered at a clinically reasonable rate. The self-injection device may include an activator for engaging the drive mechanism. Once engaged by the activator, the drive mechanism may passively expel fluid from the reservoir. Optionally, the aspect ratio (AR) of the housing divided by the aspect ratio (AR) of the drug-delivery portion defined by the equation $$AR = \frac{L3}{\sqrt{L1^2 + L2^2}}$$

is at least 100%.

In accordance with yet a further embodiment of the present invention, a system for self-injection includes a self-injection device having a housing having an interior volume and a drug delivery portion having a volume enclosed within the housing. The drug delivery portion includes a reservoir containing a fluid to be delivered to a user, and a microneedle in fluid communication with the reservoir and extendable through the housing. The drug delivery portion further includes a drive mechanism for expelling fluid from the reservoir through the microneedle. The system also includes an external controller in communication with the drive mechanism deployable to initiate expulsion of the fluid from the reservoir through the microneedle.

In certain configurations, the drive mechanism of the self-injection device is activated by a signal sent from the external controller. Optionally, the self-injection device sends a signal to the external controller when the expulsion of the fluid from the reservoir is substantially complete.

In accordance with one particular embodiment of the invention, the greatest dimension, such as the longest length of the device, is not more than two times the length of an average human hand from the end of the wrist to the tip of the middle finger. In one particular embodiment, the length of the device in the longest dimension is not more than 38 cm.

In accordance with an embodiment of the present invention, the needle of the drug delivery portion is configured for intradermal injection. Optionally, the needle is configured to extend from the housing about 2 mm allowing an injection to a depth of 2 mm. In another configuration, the needle is configured to extend from the housing about 1 mm allowing an injection to a depth of 1 mm.

In another configuration of the drug delivery portion, the fluid containing reservoir contains a single dose of a therapeutic agent. Further, the drive mechanism expels fluid from the reservoir as a single continuous dose delivered at a standard clinical dose rate. Optionally, the dose delivery time is about 10 seconds.

According to another embodiment of the present invention, the drug delivery component of the injection device further includes an activator for engaging the drive mechanism. Once engaged by the activator, the drive mechanism may passively expel fluid from the reservoir. The activator may be located on the housing of the device. Alternatively, the activator is triggered by an activation activity performed by a user on an external device such as a smart phone or other remote deployment.

In another embodiment of the self-injection device, the device further includes an indicator which alerts a user when the fluid has been fully expelled from the reservoir completing the injection. Optionally, the indicator is an external indication appearing on an external device such as a smart phone or other remote deployment device.

In another configuration of the reservoir of the drug delivery portion of the device, the drug delivery portion further includes a pierceable septum located on a wall of the reservoir for accessing the reservoir during filling. Optionally, the pierceable septum is self-sealing.

In accordance with another embodiment of the present invention, an intradermal injection device includes a non-traditional activation mechanism for initiating expulsion of a fluid from a housing, a mechanism for reducing the perception of pain in the recipient of the fluid expelled from the housing, and/or a feedback mechanism for externally providing information regarding the completion of the expulsion of fluid from the housing to the patient.

In one configuration, the feedback mechanism includes an end-of-dose indication. In another configuration, the feedback mechanism includes transmission of information regarding completion of treatment to a third party.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

FIG. 3F is a perspective view of the activator of FIG. 3D being held by a user in accordance with an embodiment of the invention.

FIG. 4A1 is a top view of the self-injection device of FIG. 4A in accordance with an embodiment of the present invention.

FIG. 4A2 is a side view of the self-injection device of FIG. 4A in accordance with an embodiment of the present invention.

FIG. 13A is a perspective view of the back housing of a module for use with an autoinjector as is known in the prior art.

FIG. 13B is a perspective view of a front portion of the module of FIG. 13A.

FIG. 14A is a top view of the external housing of a self-injection device having a miniaturized drug delivery portion in accordance with an embodiment of the present invention.

FIG. 14B is a side view of the external housing of the self injection device of FIG. 14A in accordance with an embodiment of the present invention.

DESCRIPTION OF THE PREFERRED EMBODIMENTS

Figure 1A:
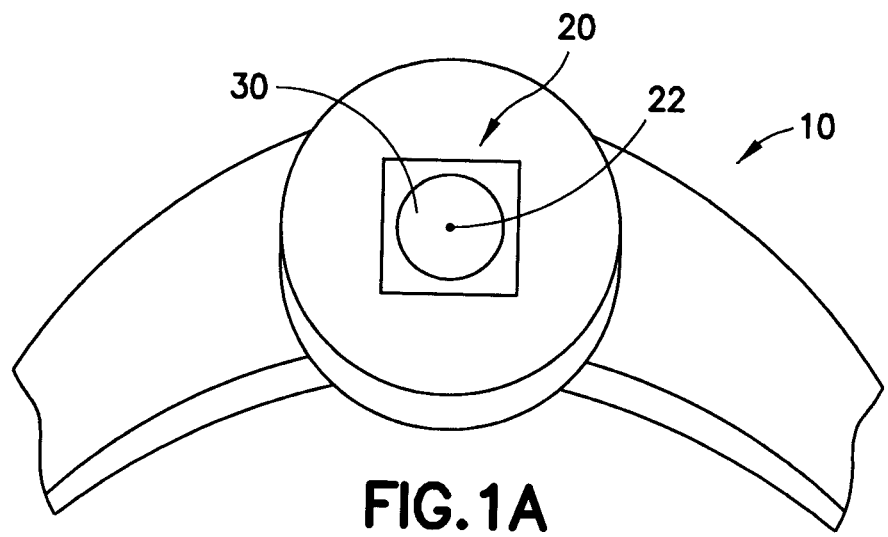
FIG. 1A is a perspective view of a self-injection device having a miniaturized drug delivery portion in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary.

It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Existing drug delivery devices, whether designed for intra-muscular, intradermal, or transdermal injections are designed based on functional considerations, specifically focusing on the elements of the device needed for drug delivery. The precise design of the "functional" elements is usually based on a set of techno-economic constraints associated with the primary function of drug delivery. The present invention recognizes that devices designed primarily based on aesthetic and human considerations, rather than functional concerns, are more enticing to users thereby increasing the likelihood that a user will attentively follow a treatment regime using the device.

More specifically, human factors which impact a person's response to a syringe or injection device could include the ease of using the device for individuals without medical training, user confidence that the injection is error-free, and user confidence that the entirety of the dose was administered. Additional non-functional features include gripping and handling features to permit more secure handling of the device, optimization of the position of the activation mechanism, clear and obvious end-of-dose indication, and, more generally, any ornamental element that reduces user fear associated with operation of the device.

Human factors may also include those elements of the device that attract potential users to perform preventative or optional medical procedures with the injection device. Unlike the human factors described above that reflect existing patient preference of one device over another, human factors for preventative or optional medical procedures reflect not only that the device is superior to other injection options, but also that the device makes an optional injection seem desirable. For example, human factors would convey to a potential user that the injection offers a new experience or, at least, offers a potential health benefit. To attract potential users to perform preventative or optional procedures, the drug delivery device should look nothing like a traditional syringe. The user should associate the appearance of the device with health and wellness rather than with a necessary medical activity often performed by a trained medical professional.

The present invention further recognizes that the Aspect Ratio (AR) is a valuable parameter for comparing the shape of two injection devices in order to determine whether the housing and functional portions of a self injection device are similar in shape.

AR is essentially a measure of whether the volumetric dimensions (height, width, depth) of an object, or more specifically the smallest rectangle parallelepiped which encloses the object, are similar in size. AR is defined as:

$$AR = \frac{L3}{\sqrt{L1^2 + L2^2}}$$

wherein L1, L2, and L3 are the lengths of the dimensions of the smallest parallelepiped which encloses the object and wherein L1≤L2≤L3. The AR of a cube or sphere is, for example, 0.707. The AR value of a number of injection devices described elsewhere herein, some of which are known in the prior art, are depicted in Table 1.

TABLE 1

|  | L1 | L2 | L3 | Aspect ratio | R | R[1] |
|---|---|---|---|---|---|---|
| Standard Syringe | 11.000 | 13.800 | 120.400 | 6.822 | 100.00% | 100.00% |
| 100 μl glass chip | 8.000 | 20.000 | 20.000 | 0.928 | 100.00% | 100.00% |
| Conventional Micro-infusor Functional Part | 16.000 | 40.000 | 65.000 | 1.509 | 100.00% | 100.00% |
| Conventional Second Micro-infusor Functional Part | 10.000 | 10.000 | 20.000 | 1.414 | 100.00% | 100.00% |
| Conventional Physioject Device | 24.300 | 24.300 | 147.700 | 4.298 | 81.52% | 63.00% |
| Conventional Physioject Device with Handle | 31.000 | 31.000 | 147.700 | 3.369 | 81.52% | 49.38% |
| Conventional Micro-infusor | 24.000 | 42.000 | 70.000 | 1.447 | 92.86% | 95.91% |
| Conventional Second Micro-infusor | 26.000 | 26.000 | 52.000 | 1.414 | 38.46% | 100.00% |
| NEO Injection device | 19.600 | 49.000 | 99.340 | 1.882 | 20.13% | 202.73% |
| Injection Device Resembling a Bracelet | 12.000 | 14.000 | 65.000 | 3.525 | 30.77% | 379.67% |
| Injection Device Resembling a Watch | 11.000 | 40.000 | 50.000 | 1.205 | 40.00% | 129.81% |

For example, a standard ink pen has an aspect ratio (AR) of about 5 to 10, depending on its diameter, whereas a standard chopstick has an aspect ratio (AR) of about 30 to 40. In contrast, an injection device according to the present invention, such as a layered glass surface having a reservoir and injection structure, has an aspect ratio of 0.928. A comparison of the AR values of objects indicates that a sphere (AR=0.707) looks more like a cube (AR=0.707) than like a chopstick (30-40). Therefore, AR values allow a "classification" of objects to determine whether two objects are related, and, consequently, whether one object exhibits higher design aesthetic over a purely functional shape.

Self injection devices in which the functional and housing portions are similar in shape are designed primarily based on functional considerations. Devices in which the shape of the housing and the functional portion are significantly different are designed based primarily on aesthetic and human considerations. Devices in which the design of the functional portion and the non-functional portion are similar are designed based primarily on functional considerations. The present invention recognizes that users without medical training feel more comfortable using a device that was designed based primarily on human and aesthetic, rather than functional, concerns. Devices designed based on these non-functional (i.e., human and aesthetic elements) are more attractive to users and can be used more confidently by those without medical training.

Table 1 also lists the R value for each injection device. The R value is the ratio of the L3 length of the functional (e.g., drug delivery) portion of the device and the L3 length of the non-functional or housing portion of the device, according to the equation:

$$R = \frac{L3_{Functional\_portion}}{L3_{housing}}$$

The "Functional portion" refers to the elements of the device necessary for fluid injection. In a typical injection syringe, "Functional portions" include the delivery structure such as a needle, the reservoir for containing the liquid drug, and an expulsion mechanism, such as a plunger. An essentially artistic object, such as a sculpture, has an R value of near 0.

Table 1 also includes an $R^1$ value for each injection device. $R^1$ is defined as the ratio of the AR of the external housing of the device over the AR for the functional elements of the device. The formula for $R^1$ is:

$$R^1 = \frac{AR_{Housing}}{AR_{FuntionalPart}}$$

Figure 12A:
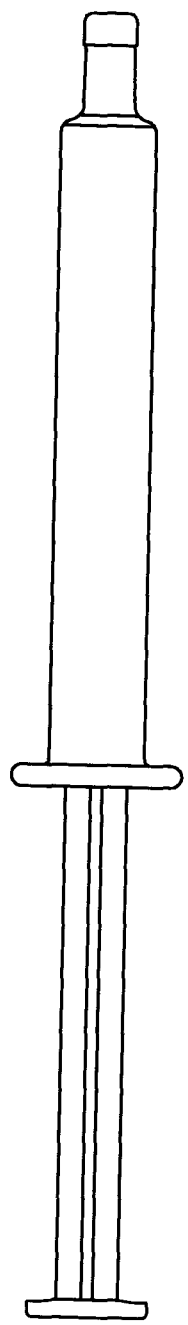
FIG. 12A is a perspective view of a conventional syringe as is known in the prior art.
Figure 12B:
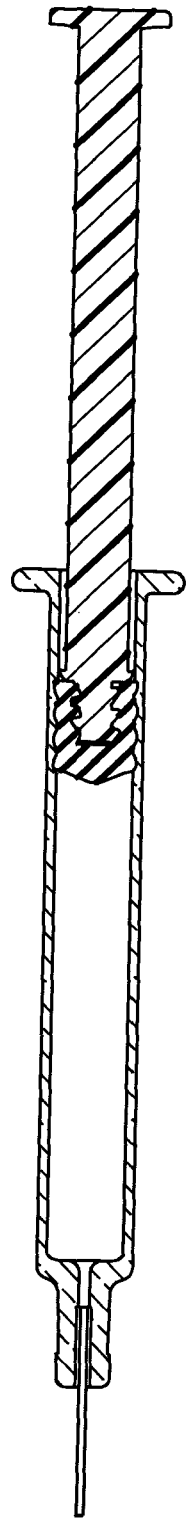
FIG. 12B is a cross-sectional view of the syringe of FIG. 12A.
Figures 13C, 13D:
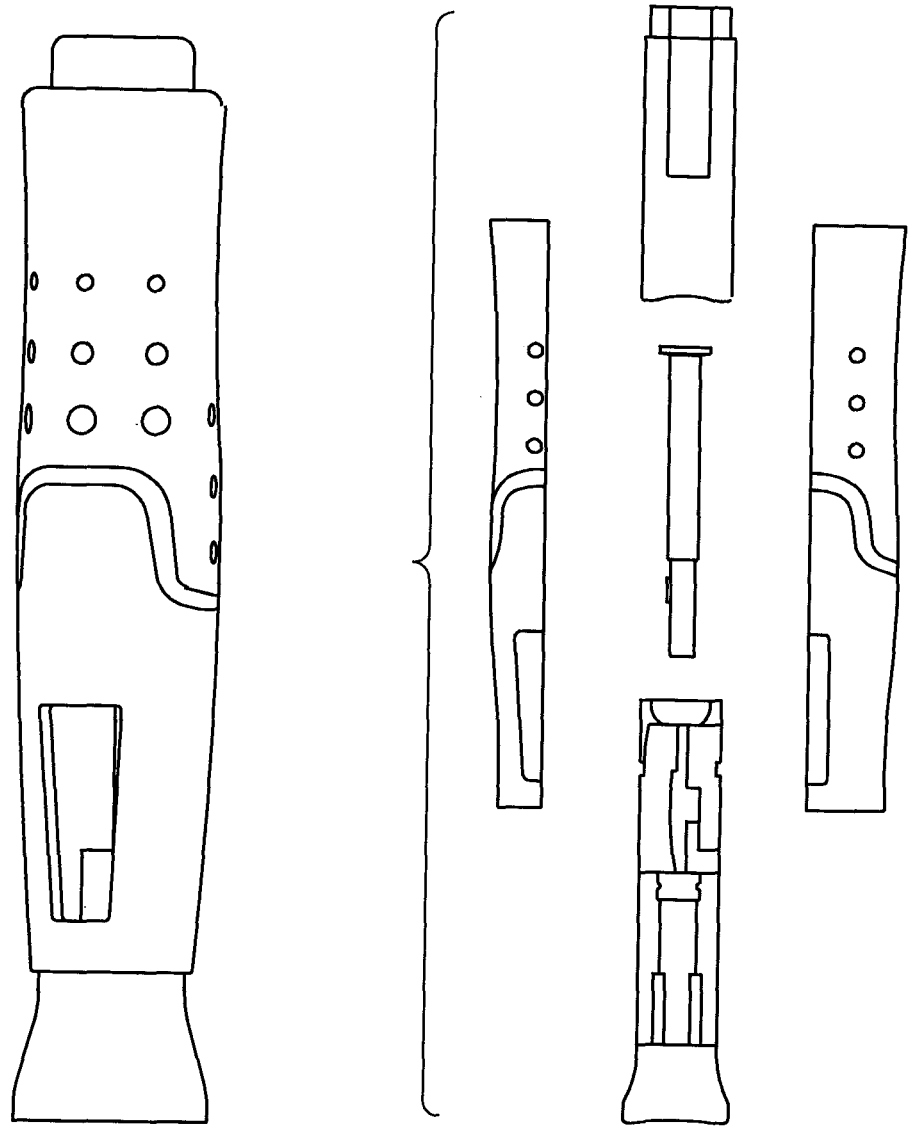
FIG. 13C is a perspective view of the module of FIGS. 13A and 13B as is known in the prior art.
FIG. 13D is an exploded view of the module and autoinjector of FIG. 13C as is known in the prior art.
Figure 18:
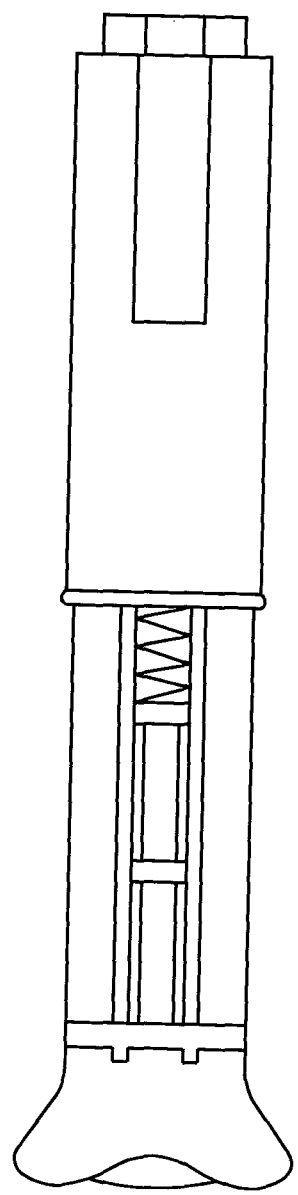
FIG. 18 is a perspective view of a physioject autoinjector as is known in the prior art.

A standard syringe, as depicted in FIGS. 12A and 12B, is an injection device including only functional elements. With reference to FIG. 18, an example Physioject™ autoinjector is a disposable autoinjector for a prefilled syringe. A handle element can also be included with the autoinjector as is depicted in FIGS. 13A-13D. Most observers would recognize that a standard syringe and a Physioject™ autoinjector have the same general overall shape. Not surprisingly, comparison of the AR values for a syringe and a Physioject™ autoinjector confirms this observation. The AR value for a syringe and the Physioject™ autoinjector are large and closely related (3.3 and 4.2, respectively). The present invention recognizes that most individuals would appreciate that objects having an AR value that differ by less than 50% have essentially the same overall shape. Accordingly, the present invention also recognizes that self-injection devices having an AR value that differ by less than 50% were most likely designed based on the same considerations.

With reference to FIGS. 13A-13D and 18, the Physioject™ autoinjector and Physioject™ autoinjector with handle devices do include features that make injection easier for a user such as a triggering mechanism and trigger button that releases the needle and initiates the injection. As a result, the AR of the Physioject™ autoinjector and standard syringe are not identical. Instead, the $R^1$ values for the Physioject™ autoinjector is 49.38% and the $R^1$ value for the Physioject™ autoinjector with handle is 63.00%. However, since the $R^1$ values for the Physioject™ autoinjector and the Physioject™ autoinjector with handle are within about 50%, it is evident that both the Physioject™ autoinjector and the Physioject™ autoinjector with handle devices and standard syringes generally have the same shape and were designed based primarily on the constraints of the functional element of the device.

With respect to FIGS. 13A-13D, it is noted that the Physioject™ autoinjector with handle does include an enhanced handle and trigger structure for improving handling of the device. The enhanced handle is an element that makes the device more attractive for users (e.g., human factors) by offering a better "look and feel". Notably, the improved gripping of the handle gives users confidence that they are holding the device correctly and that the device will not slip out of their hands during use. As a result of the improved appearance, the device also looks less intimidating further reducing a user's concerns about performing an injection. Since the handle is not related to the primary function of fluid injection, the enhanced handle is a non-functional element of the device.

The diameter of the handle of the Physioject™ autoinjector with handle is enlarged compared with the standard Physioject™. Consequently, as expected, the AR and $R^1$ values for the Physioject™ autoinjector with handle are reduced compared with the standard Physioject™. However, since the $R^1$ value is still within about 50% of the $R^1$ value of the standard syringe, the Physioject™ autoinjector with handle has "essentially" the same shape as a standard syringe and was designed based primarily on functional considerations.

Figure 19A:
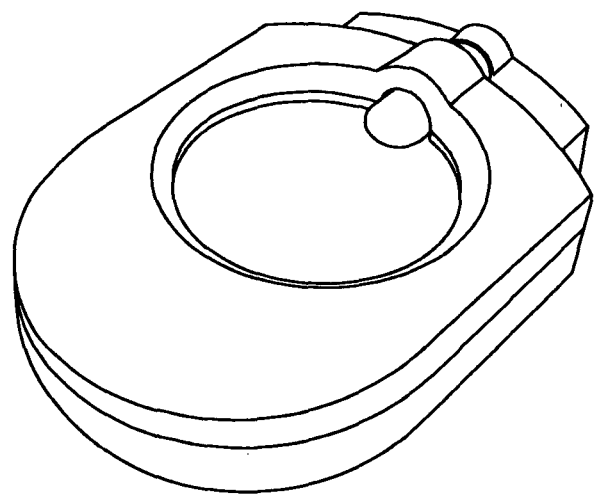
FIG. 19A is a perspective view of a micro-infuser in accordance with an embodiment of the present invention.
Figure 19B:
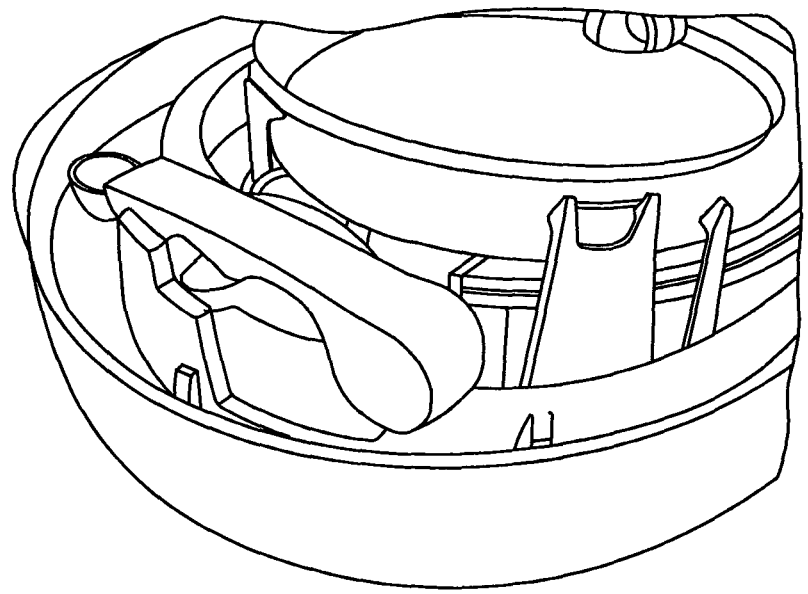
FIG. 19B is a perspective enlarged partial view of the micro-infuser of FIG. 19A in which the top cover is translucent so that internal elements of the device are visible.

With reference to FIGS. 19A and 19B, a conventional micro-infusor device is an injection device which includes a 5 mL reservoir containing a fluid to be injected. The AR values for the functional part (e.g., the 5 mL reservoir) of the conventional micro-infusor and for the overall conventional micro-infusor device are shown in Table 1. The $R^1$ value for the conventional micro-infusor is close to 100% (95.11%) indicating that functional considerations strongly control the design of the device. As shown in FIG. 19B, the functional elements of the conventional micro-infusor extend almost to the external housing. In other words, the smallest parallelepiped enclosing the functional elements is nearly identical in size and shape to the smallest parallelepiped enclosing the entire device.

Figure 20A:
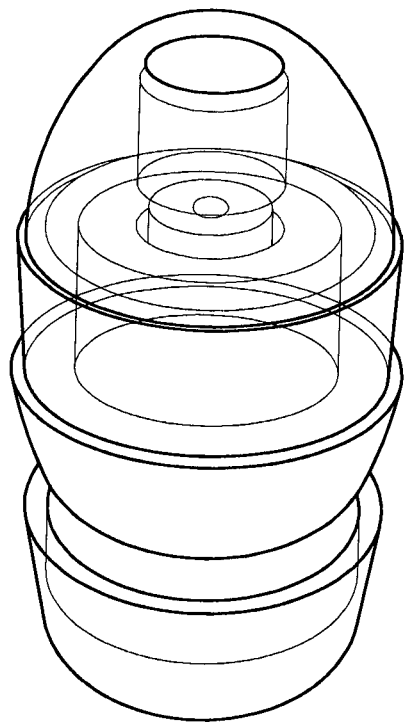
FIG. 20A is a perspective view of an injection device as is known in the prior art.
Figure 20B:
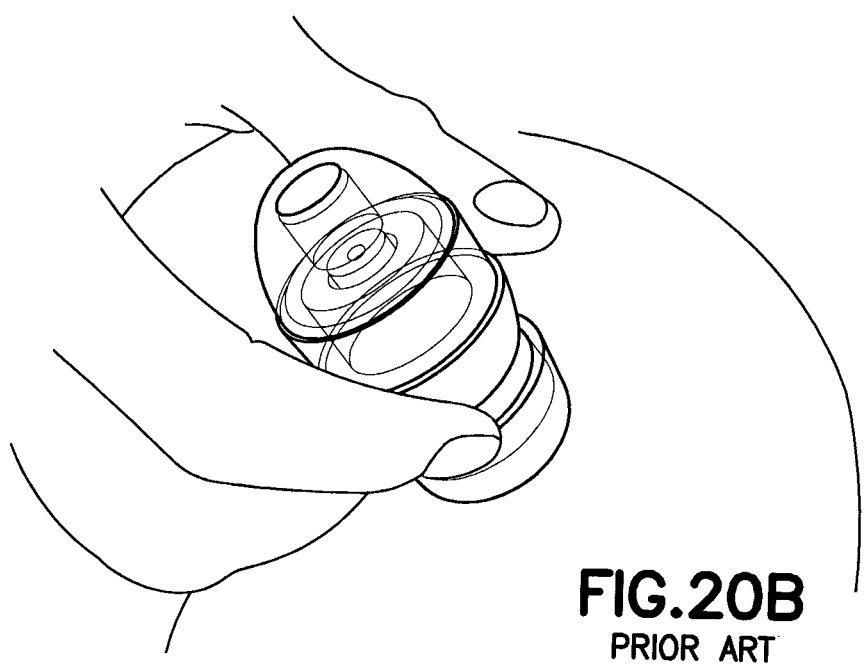
FIG. 20B is a perspective view of the injection device of FIG. 20A being used by a patient.

With reference to FIGS. 20A and 20B, a second micro-infusor device is shown as another drug delivery device without a syringe as the functional element. As is depicted in FIG. 20A, the device is roughly an elongated sphere and is adapted to be pressed against the skin for injection. The AR of the functional part of the second micro-infusor device is 1.414. The AR of the functional portion is identical. Therefore, it may be assumed that the external housing and internal functional portion of the second micro-infusor device have the same shape.

As shown by the above exemplary devices, for devices designed around a syringe, the aspect ratio (AR) of the housing is likely to be smaller than the aspect ratio (AR) of the syringe. It is believed that this is the case because the syringe was originally designed for use without additional elements such as auto-injectors or injection pens. Therefore, the syringe is already about the size of the hand and can already be comfortably held by an average user. Therefore, it is unlikely that any added elements, such as enhanced handles, will increase the length by an appreciable amount. Increasing the length would make the device more difficult to hold and manipulate while performing an injection. Thus, the length (L3) remains essentially the same for a standard syringe and for devices designed around syringes, such as autoinjectors. For devices designed around standard syringes, the overall volume of the device is increased around the barrel, thereby increasing the dimensions of lengths L1 and/or L2. As a result, the AR for a device designed around a syringe is smaller than for a standard syringe, and thus the $R^1$ ratio will be smaller than 1. Therefore, it has been determined that for devices designed around syringes, such as an autoinjector, the $R^1$ value is less than 100%.

In contrast, for injection devices having a miniaturized drug delivery portion fabricated using micro-scale batch processing technology, the external design of the non-functional portion is not based on the shape of the functional portion. Therefore, the $R^1$ value is greater than 100%. For example, with respect to FIGS. 1A-2D, the AR of the injection device resembling a bracelet is 3.525, which is within an order of magnitude of the AR values of several devices designed around syringes, such as the Physioject™ autoinjector (AR=4.298) and the Physioject™ autoinjector with handle (AR=3.369). However, the $R^1$ values of these devices designed around syringes are all lower than 100%. This is the direct consequence of the fact that for the injection device resembling a bracelet, as shown in FIGS. 1A-2D, the aspect ratio of the functional portion, is very small (AR=0.928). Accordingly, the $R^1$ value for the injection device resembling a bracelet is large. The functional part of the injection device resembling a bracelet has been created to fit within a pre-existing designed object, namely the external housing. The present invention recognizes that all devices designed in this way, focusing first on the external housing, will have an $R^1$ ratio greater than 100%.

Figure 14C:
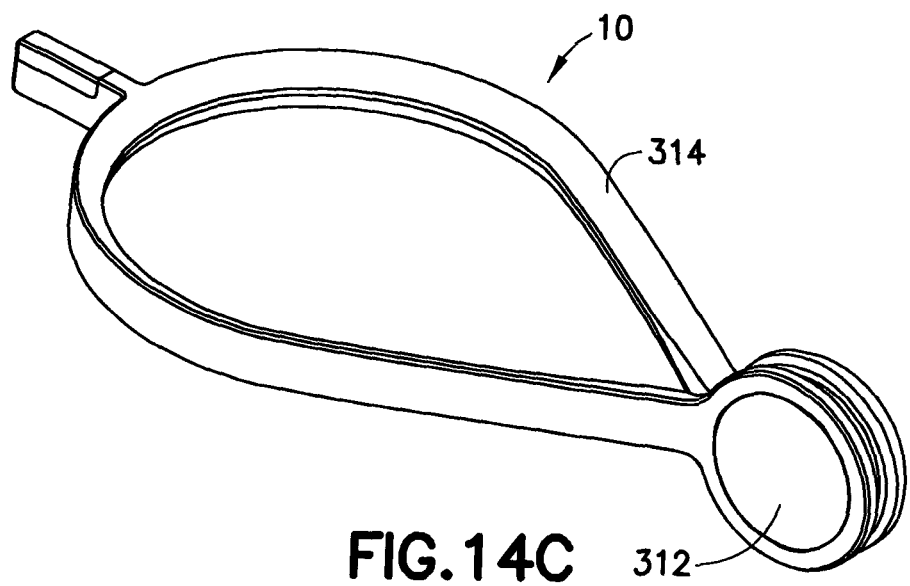
FIG. 14C is a perspective view of the external housing of FIG. 14A in accordance with an embodiment of the present invention.
Figure 14D:
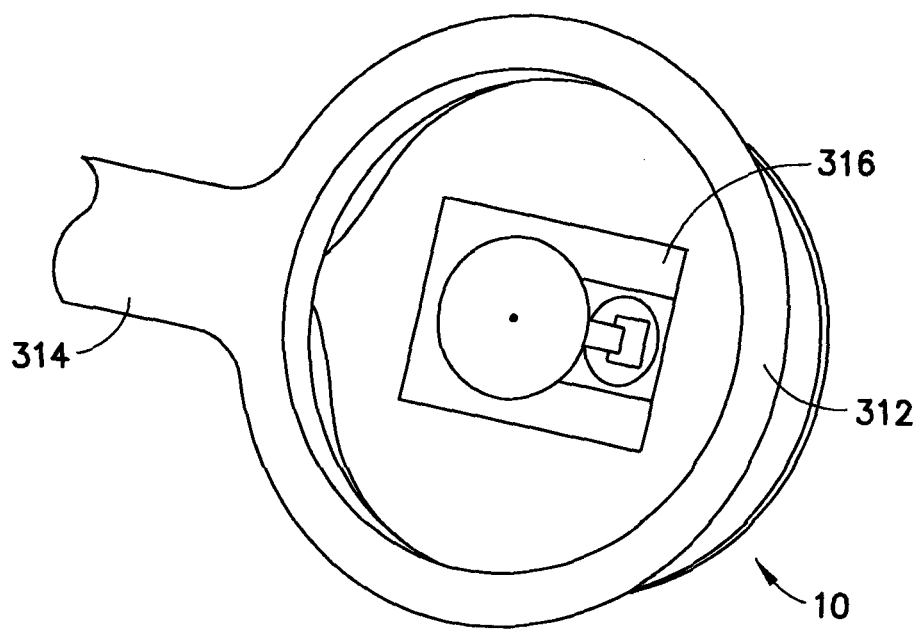
FIG. 14D is an enlarged partial view of the external housing of FIG. 14A including the drug delivery portion of FIG. 6B in accordance with an embodiment of the present invention.
Figure 15A:
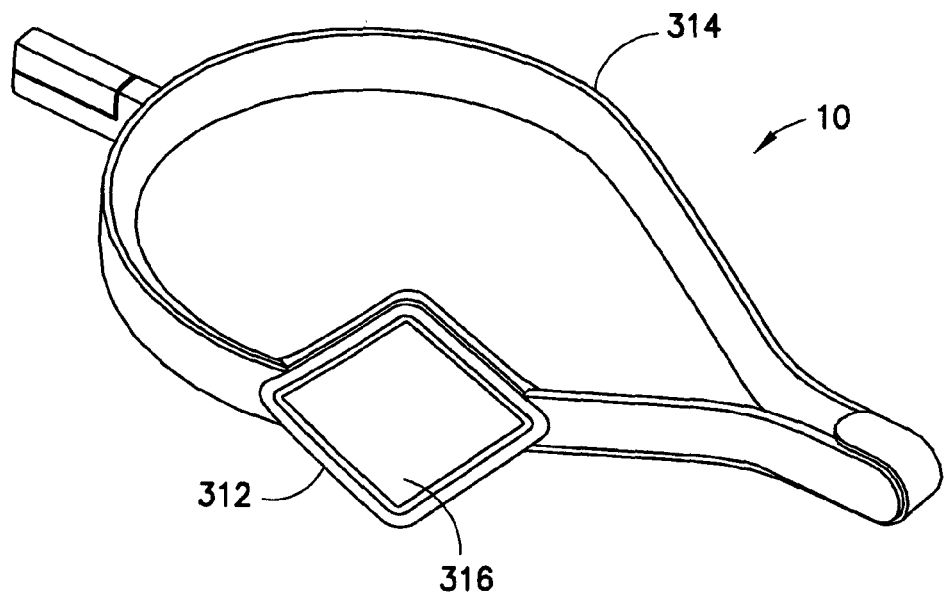
FIG. 15A is a perspective view of the external housing of a self-injection device in accordance with an embodiment of the present invention.
Figure 15B:
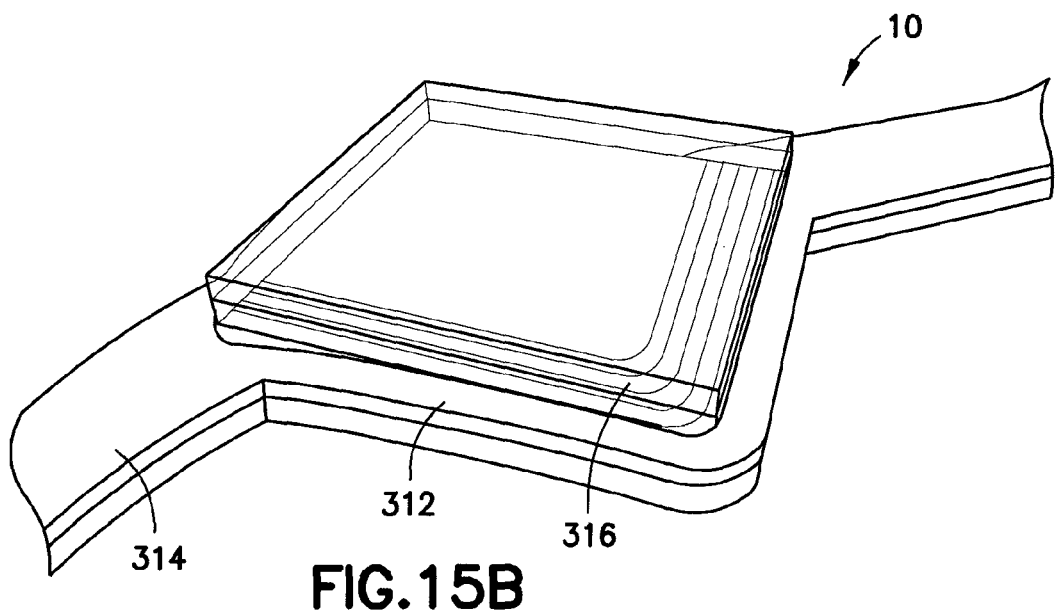
FIG. 15B is an enlarged partial perspective view of the external housing of FIG. 15A containing the drug delivery device of FIG. 6B in accordance with an embodiment of the present invention.
Figure 15C:
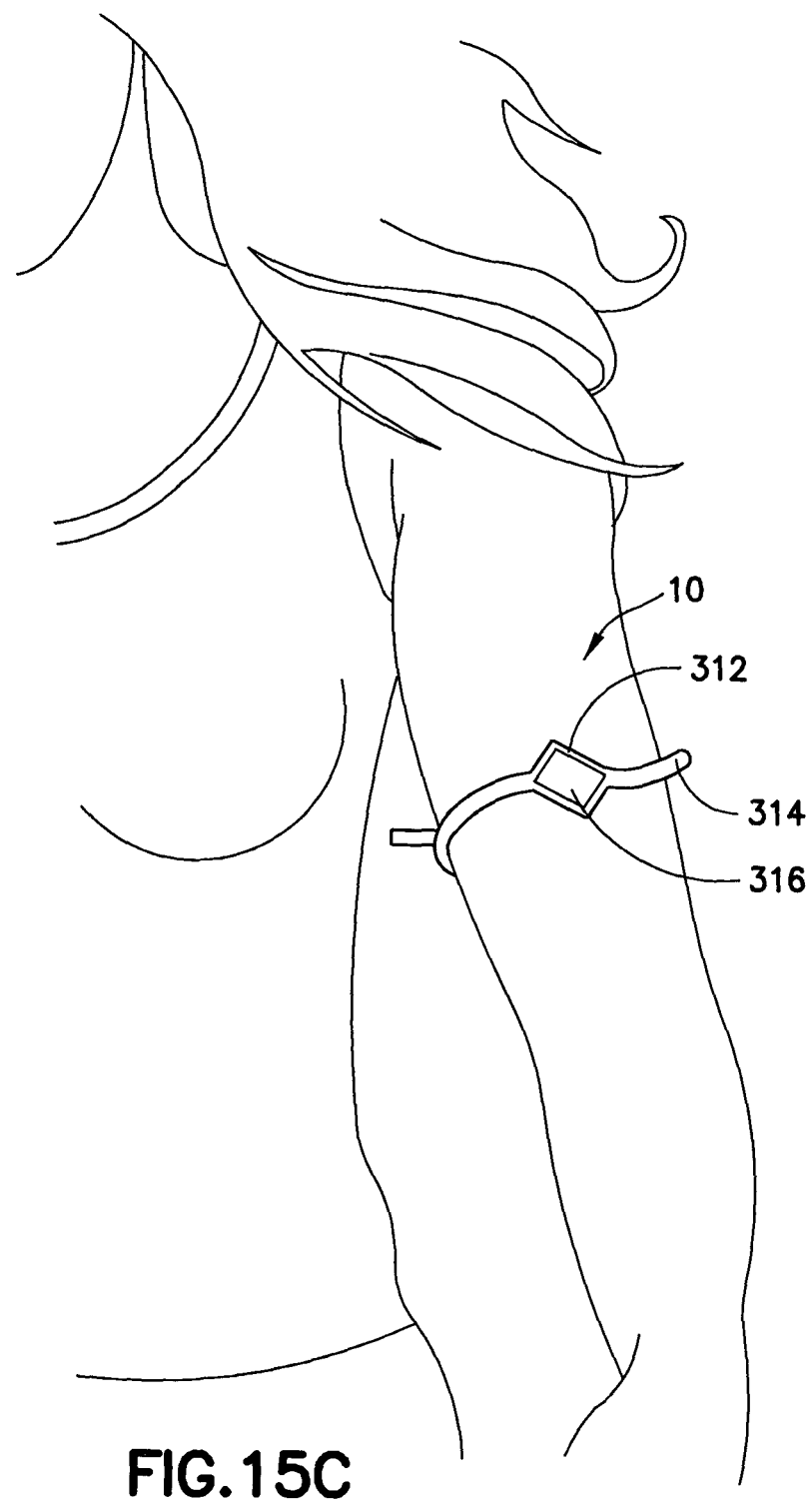
FIG. 15C is a photographic representation of the self-injection device of FIG. 15A in accordance with an embodiment of the present invention being worn by a user.
Figure 16:
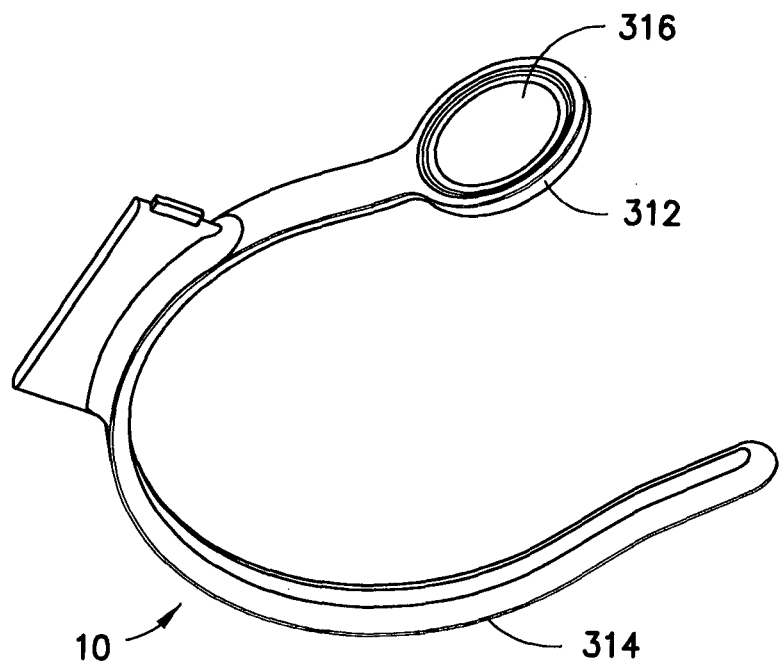
FIG. 16 is a perspective view of a self-injection device in accordance with an embodiment of the present invention.
Figure 17:
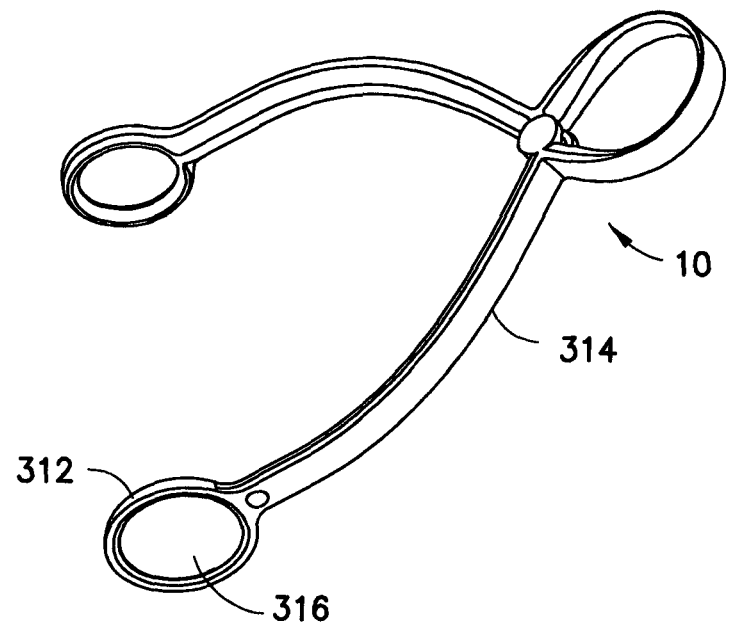
FIG. 17 is a perspective view of a drug delivery device according to another embodiment of the present invention.

With reference to FIGS. 14A-14D, the present injection device 10 (the "NEO" device") includes a functional element 316 deposited on a miniaturized glass chip comprising a reservoir, an actuator, and a needle. A number of embodiments of the miniaturized glass chip are depicted in FIGS. 5-9B and described in greater detail below. The AR value of the glass chip of the device is 0.928. The external housing of the "NEO" injection device includes one or more housing brackets 312 that contain a functional element 316, such as a drug delivery portion, as shown in FIG. 14D. The drug delivery portion 316 may be a glass wafer fabricated by a micro-scale batch processing technique. The housing brackets 312 are connected by a curved band 314, which is designed to resemble the appearance of headphones, a design that users are already familiar and comfortable with. The AR value of the external housing is 1.882 and the $R^1$ ratio of the device is 210.45%. The increased $R^1$ indicates that the external housing of the "NEO" device is highly dissimilar from the shape of the functional portion, namely the miniaturized glass chip. Therefore, it is apparent that the "NEO" was not designed primarily based on functional considerations. Instead, the "NEO" was designed based primarily to realize human and aesthetic factors. The present invention recognizes that devices that are designed primarily based on human and aesthetic factors are more appealing to users and are more likely to encourage users to perform self-injection.

However, it is recognized that a device with an $R^1$ value greater than 100% could also be realized by taking a syringe and embedding it into a large arbitrary shape. In the case of a standard syringe and an autoinjector, the AR of the autoinjector would need to be about 14.35 for the device to have the same $R^1$ value as the "NEO" device. To achieve an AR value of 14.35, an autoinjector having the same diameter as the syringe would have a longest length (L3) of about 2.12 meters. An autoinjector having a length of over 2 meters would be unusable. To ensure that the device is not so unwieldy as to prevent use by the average user, according to one embodiment of the invention, the longest dimension (L3) of the self injection device is no longer than twice the length of a human hand. In one embodiment, the maximum length is defined as 38 cm. Alternative embodiments of the "NEO" device having a similar appearance and similar design elements are depicted in FIGS. 15A-17.

With reference now to FIGS. 1A-4B, alternative embodiments of self-injection devices having external housings 10 designed primarily to address "human factors" are depicted. The housing 10 can have numerous potential forms including an external shape resembling buttons, bracelets, stickers, or patches. The housing may also be formed and configured with functional components which serve another purpose such as a wrist watch for keeping track of time.

Figure 1B:
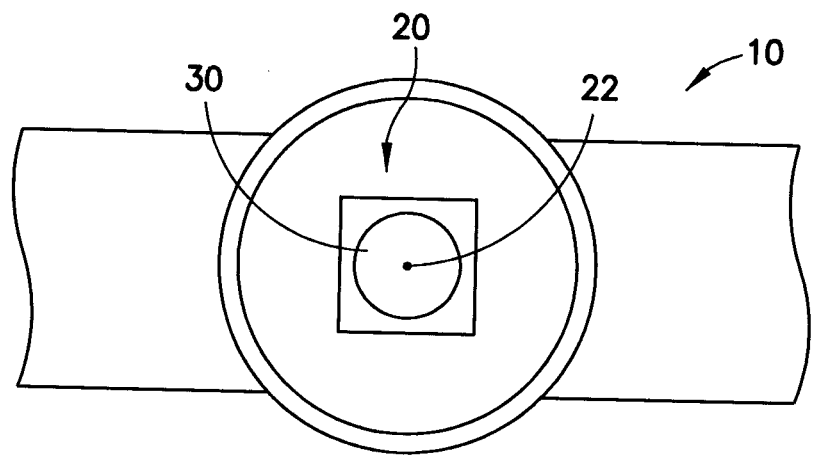
FIG. 1B is a top view of the self-injection device of FIG. 1A in accordance with an embodiment of the present invention.

With reference to FIGS. 1A and 1B, a self-injection device resembling a "bracelet" is depicted. The "bracelet" includes a housing 10 and a functional delivery portion 20. The shape of the housing 10 (i.e., the non-functional portion) is indicated by a cross-hatch design. The drug delivery portion 20 includes a reservoir 30 and a needle 22 that is not cross-hatched. The needle may be a mini-needle, such as a 30 gauge needle for intradermal injection, or a larger needle for subcutaneous or intramuscular injection. It is noted, however, that FIGS. 1A and 1B are only schematic drawings of one embodiment of the device. The dimensions of the delivery portion 20 and housing 10 are not drawn to scale and are not intended to convey the actual shape relationship between the two portions of the device. As noted above, the desired $R^1$ value is greater than 100%.

Figure 2A:
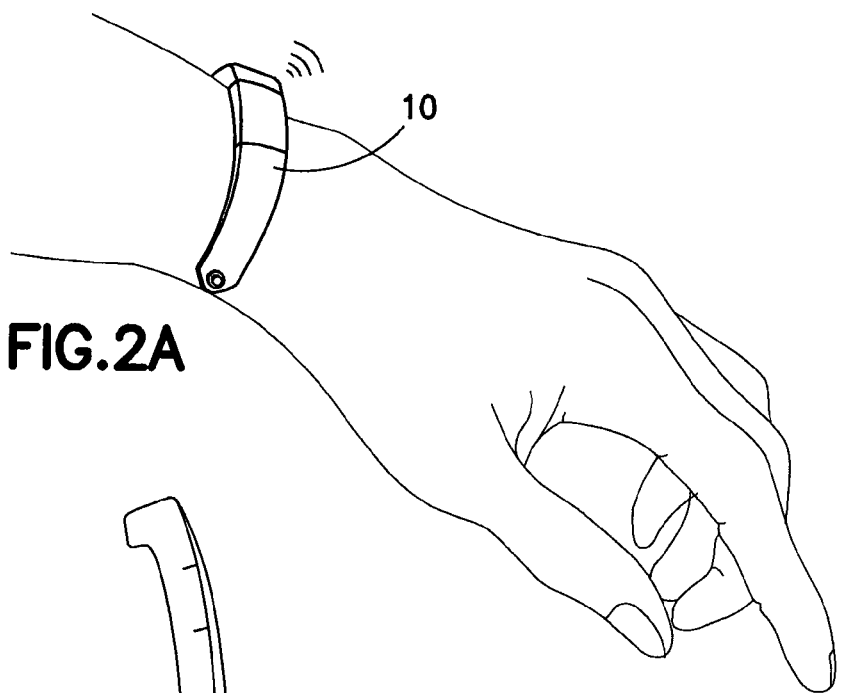
FIG. 2A is a perspective view of the self-injection device of FIG. 1A being worn by a patient in accordance with an embodiment of the present invention.
Figures 2C, 2D:
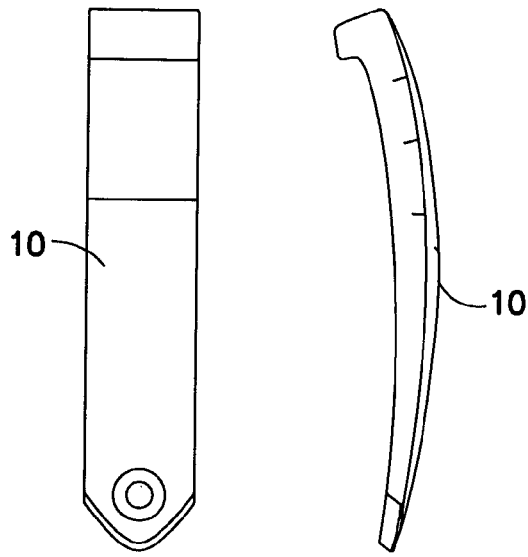
FIG. 2C is a top view of the self-injection device of FIG. 2A in accordance with an embodiment of the present invention.
FIG. 2D is a side view of the self-injection device of FIG. 2A in accordance with an embodiment of the present invention.
Figure 4A:
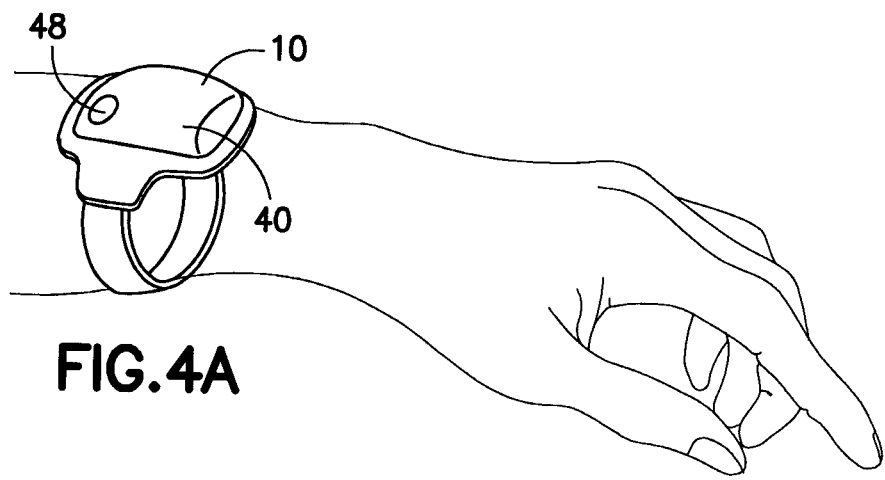
FIG. 4A is a perspective view of a self-injection device in accordance with an embodiment of the present invention.
Figure 4B:
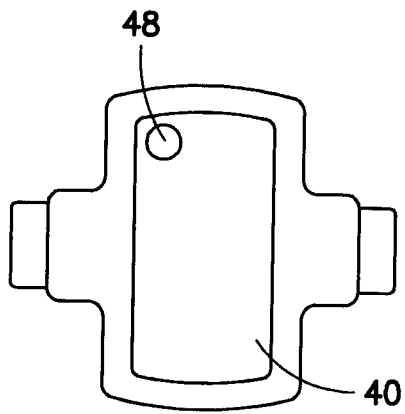
FIG. 4B is a photographic representation of the self-injection device of FIG. 4A being worn by a patient in accordance with an embodiment of the present invention.
Figure 4B:
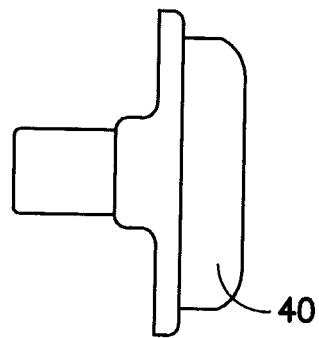
Figure 4B:
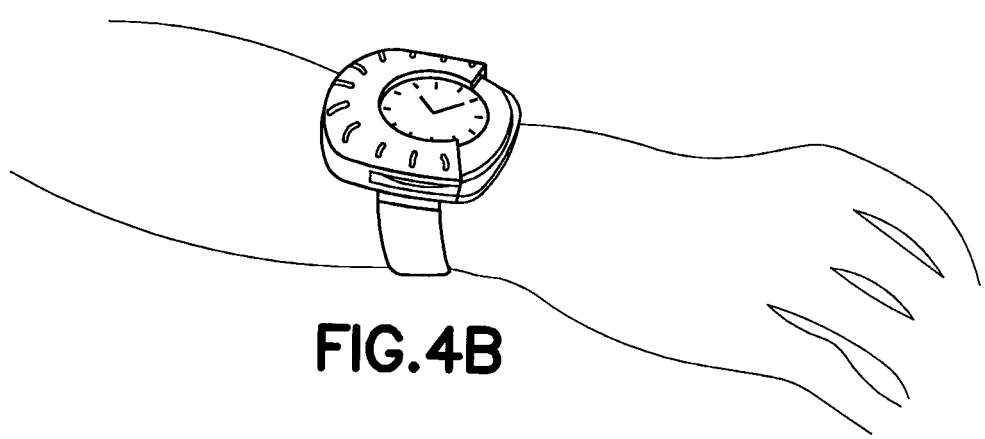

Additional non-limiting embodiments of types of housings which can be used with the device of the present invention are depicted in FIGS. 2A-4B. The housing 10 of FIGS. 2A and 2B is a bracelet designed to engage with the forearm of a user. The bracelet design is meant to provide comfort to users by closely resembling an activity with which he or she is already familiar, namely taking off and removing a piece of jewelry. The bracelet housing 10 includes an ornamental squiggle which can be an indicator 48 to alert the user when the injection is complete. With reference now to FIGS. 3A-3G, a delivery device may include a housing 10 in the shape of a small pod or button to be applied to the arm of a user. The high-tech appearance of the delivery device is meant to inspire confidence by resembling other high-tech devices that the user is already familiar with and which the user already associates with power, precision, and accuracy. The housing 10 of the button further includes an activator 40 and an end-of-dose indicator 48. With reference now to FIGS. 4A and 4B, the delivery device includes a housing 10 in the shape of a watch patch designed to be correctly placed on the forearm of a user. The watch-shaped housing 10 is designed to be simple and familiar so that a user will associate the unusual act of self-injection with the familiar activity of wearing a watch. The watch shaped housing includes an activator 40 and an indicator 48. In each of the above-described designs, the outer housing 10 provides a resemblance to a separate device having a function entirely separate from the function of performing an injection or a vaccination.

Figure 5:
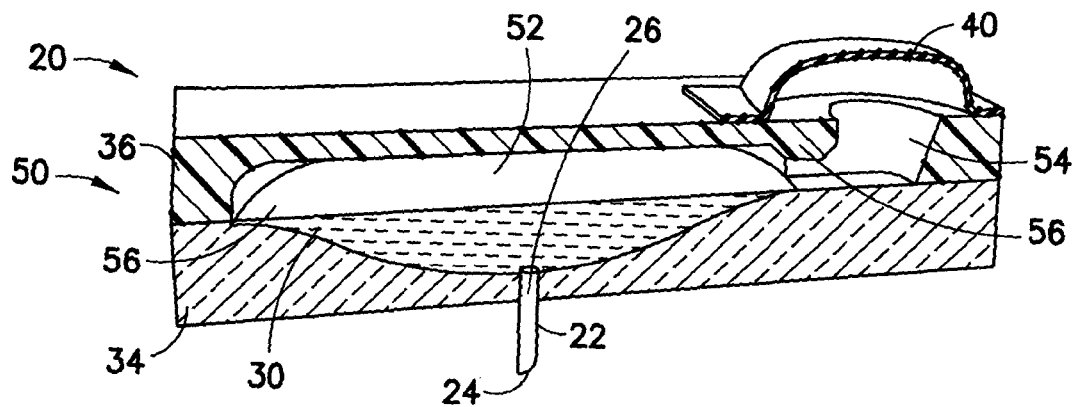
FIG. 5 is a perspective cross-sectional view of the drug delivery portion of the self-injection device of FIG. 4B in accordance with an embodiment of the present invention.
Figure 6A:
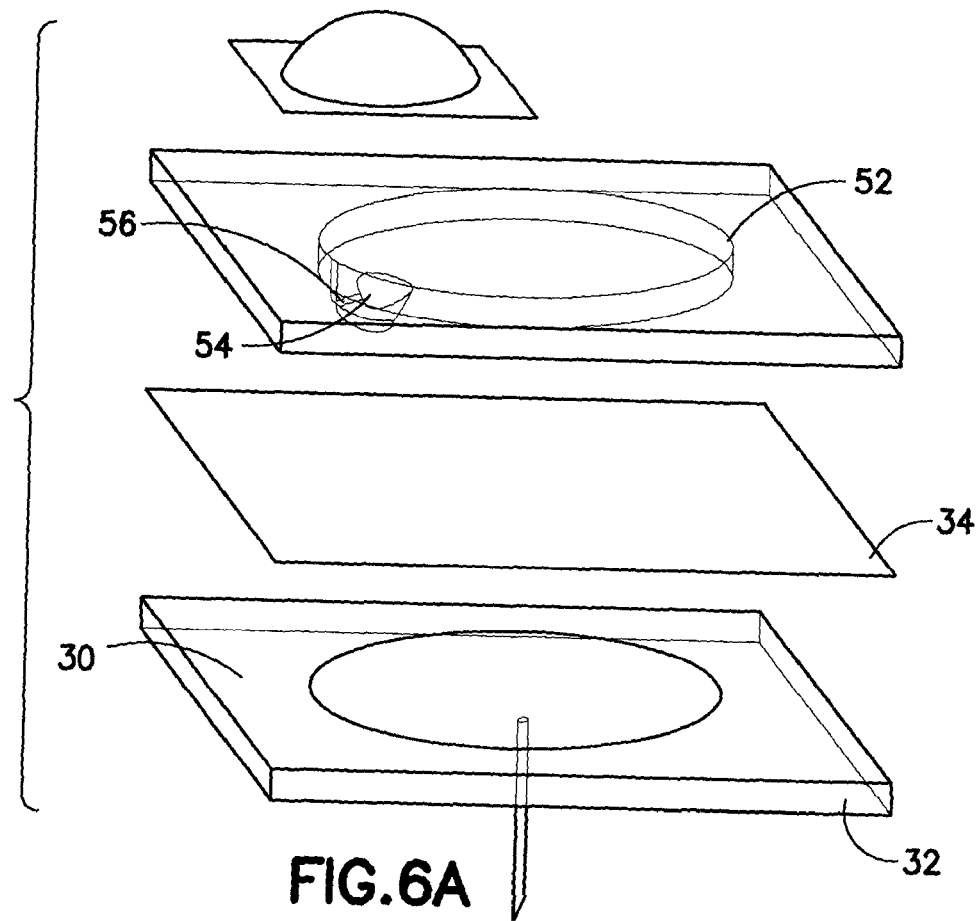
FIG. 6A is an exploded perspective view of the drug delivery portion of the self-injection device of FIG. 5 in accordance with an embodiment of the present invention.
Figure 6B:
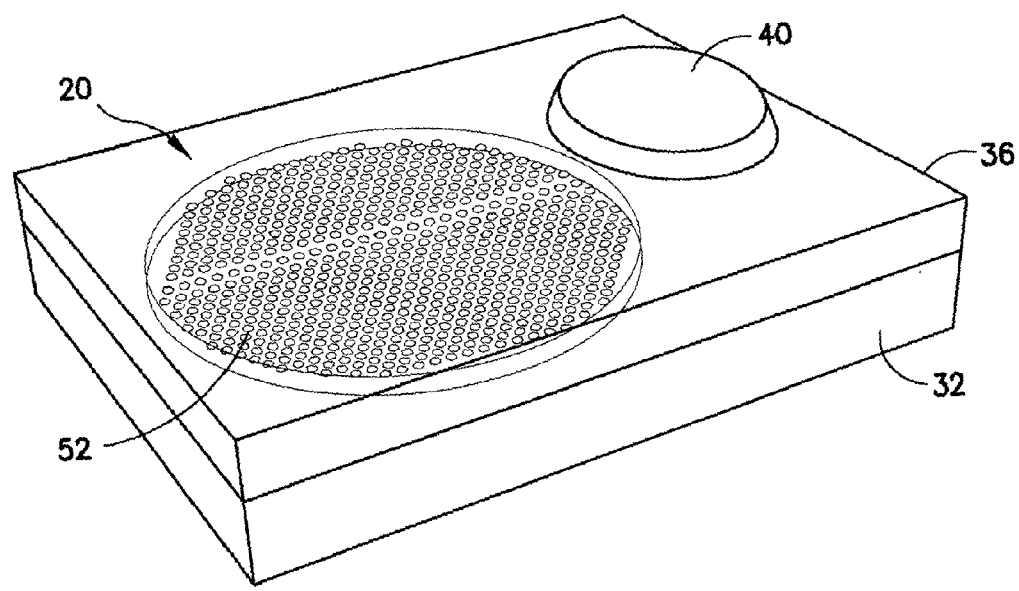
FIG. 6B is a perspective view of the drug delivery portion of the self injection device of FIG. 4B in accordance with an embodiment of the present invention having a translucent top layer so that interior elements of the drug delivery portion are visible.

With reference now to FIGS. 5-6B, the drug delivery portion 20 of the device is depicted. As described above, the drug delivery or "functional" portion of the device is defined as the minimum set of elements necessary for enabling one to fulfill the primary function of the delivery system, which is to deliver a given volume of the active ingredient at a given site, e.g., in or on the body, and possibly at a certain depth under the skin. The drug delivery portion 20 includes a delivery structure such as a needle 22 in fluid communication with a fluid containing reservoir 30. Alternative structures for facilitating fluid delivery include a catheter for injections, a straw for oral delivery, or a nozzle for nasal or pulmonary delivery. In the embodiment of FIG. 5, the needle 22 is a hollow miniaturized needle with a patient puncture tip 24 on one end of the device and an opposite end 26 in connection with the fluid reservoir 30. A lumen (not shown) extends longitudinally through the needle forming a passageway for fluid flow. The needle 22 can be formed from any material having suitable strength properties and which can be sharpened to a tip sufficient to pierce the skin of a user. Exemplary materials include metals, metal alloys, and medical grade high density polymers. While the dimensions of the needle 22 are largely dependent on the type of therapeutic agent or drug for which the apparatus is being prepared, for intradermal vaccination purposes, the needle 22 will be about 2 to 4 mm in length with a cross-sectional diameter of about 0.3 to 0.5 mm. In use, according to one embodiment of the present invention, the needle 22 extends from the base of the drug delivery portion 20 of the self-injection device by about 1 to 2 mm, allowing the needle 22 to enter the skin of a user to a depth of between 1 and 2 mm.

It is further understood that the needle 22 may be adapted to further reduce the pain of injection, thereby reducing the fear and anticipation often associated with having an injection performed. As stated above, fear and anticipation are two of the "human factors" which discourage potential users from adopting self-injection devices and techniques. Generally, pain from an injection results from the pH or ionic force of the injected solution, as well as the tearing apart of internal tissues to "free" a space within the internal tissues capable of receiving the volume of liquid injected, rather than from the injury to the skin. Therefore, pain relief methods may be used to counteract these solution forces to effectively reduce pain. For example, an anesthetic or pain reliever or analgesics could be coated on the needle 22. The pain reliever could be in the form of a hydrophobic polymer coating on the needle 22 surface which diffuses to the patient's skin following injection to relieve the pain sensation. In one embodiment, the analgesics or anesthetic, such as lidocaine, prilocaine, tetracaine, ametop gel, or tramadol, is dissolved or dispersed or emulsified in silicone oil, and the mixture is spray or dip coated on the needle. Alternatively, salts embedded on the needle surface have a similar pain reducing effect by counteracting the ionic force of the injected solution. Analgesics or other topical numbing agents, such as lidocaine, prilocaine, tetracaine, ametop gel, or tramadol, may also be applied to the patient's skin prior to performing the injection and/or vaccination to reduce the pain sensation associated with skin penetration by the needle. In a further embodiment, the needle and zone of contact with the skin may be impregnated with a numbing agent, e.g., ethyl chloride, which numbs the skin around the injection site as the material evaporates.

In each of the above-described designs, the delivery structure or needle 22 establishes fluid communication between the reservoir 30 and the patient. The reservoir 30 is emptied by an expulsion mechanism. According to one preferred non-limiting embodiment of the device, the reservoir 30 plays an active part in expulsion of fluid. For example, a plunger-type part may push the liquid out by scanning the majority of the inner volume of a rigid reservoir (e.g., a traditional syringe or cartridge, with a gliding plunger). Alternatively, a part of the reservoir 30 may be deformable and can be pressed to expel the liquid (e.g., a collapsible reservoir as in a micro-infuser). According to other embodiments of the present invention, the reservoir 30 is passive and does not contain or embody structure for expelling fluid. Instead, the reservoir merely contains the liquid, and an external pumping mechanism draws the liquid out of the reservoir.

In most areas of the body, an injection of 1 to 2 mm in depth pierces and extends through the epidermis layer of skin allowing for delivery of drug directly to the dermis. Advantageously, many therapeutic agents that cannot diffuse through the epidermis are able to diffuse through the dermis layer. It is noted, however, that the depth of the epidermis varies and is, in some areas of skin, as thick as 1.5 mm. For injection intended to be delivered in locations where skin is thicker, the puncture depth must be increased to compensate for increased skin thickness.

With continued reference to FIGS. 5-6B, according to one non-limiting embodiment of the invention, the reservoir 30 for containing a therapeutic agent is formed within a substrate layer 32 of the delivery portion 20 of the device. According to one non-limiting embodiment, the substrate is made from silicon or glass, and more generally from any material which can be patterned by lithography and etched to form a reservoir 30. The choice of material for the substrate layer 32 is driven largely by the composition of the therapeutic agent contained in the reservoir 30. Specifically, the substrate material should be non-reactive with the therapeutic agent. Glass, for example, borosilicate type 1 glass, is largely inert and non-reactive making it an excellent substrate material for many applications. Glass is also impenetrable to both water and oxygen. Alternatively, the reservoir may be a pre-manufactured structure which is affixed to the substrate layer 32. The needle 22 extends from the reservoir 30 through the substrate layer 32. The volume of the reservoir is chosen to correspond closely to the volume of a single dose of the therapeutic agent to be delivered to the user. By configuring the reservoir based on dose volume, the fluid to be injected takes up a majority of the reservoir volume leaving very little wasted space and reducing the overall size of the delivery portion 20 of the device. In contrast, with traditional syringes, the fluid may only fill a third or less of the total reservoir volume.

With continued reference to FIG. 5, the delivery portion 20 further includes an activator 40 and a fluid expulsion mechanism 50. Specifically, the self-injection device is designed to provide unusual activation and unnoticeable delivery when compared to a traditional syringe. The user actively activates the device, but the activation occurs in a manner which is different from ways in which traditional drug delivery devices are activated (e.g., pressing a piston to drive a plunger through a reservoir). Examples of "unusual" activation mechanisms include buttons or triggers located on the exterior of the device housing for a user to press. In another embodiment of the present invention, the device is activated by a command sent from an external electronic device, such as a smart phone, over a wireless connection. In that case, the self-injection device would include a wireless transmitter for sending and receiving data and instructions from the external electronic device. Numerous wireless transmission protocols for transmission of data over radio-frequencies exist which are capable of being adapted for use with the present invention. Wireless transmission protocols may include: Bluetooth, WiFi, Z-Wave, and Zig-Bee. Bluetooth is most commonly used for short range wireless transmission of a few meters or less. WiFi has a longer transmission range than Bluethooth; however, it consequently has greater power consumption requiring a larger capacity power supply to operate effectively. In addition to a smart phone, other electronic devices such as computers or tablet PCs could also be adapted to activate the self-injection device. In still other configurations, the act of applying the housing to the skin of the patient, such as putting on a bracelet or watch, may initiate activation.

In certain embodiments, the external electronic device will run a software program to manage the sending and receiving of data from the self-injection device. Optionally, the included software also records the date/time and type of injection for the user's records and sends acknowledgement that the injection has been completed to the user's doctor, pharmacy, or medical services center.

The passive injection portion of the drive mechanism enables the injection to occur with as little participation by the user as possible. By not being required to participate in traditional injection activities (i.e., injecting the needle, pushing the plunger), the user is less aware that an injection is occurring. Users who are less aware of the injection are less likely to fear the injection and, consequently, are more likely to undergo voluntary procedures such as flu shots. Numerous mechanisms for passively expelling a fluid from a reservoir for injection to a patient are within the scope of the invented self-injection device. Examples of such expulsion mechanisms are discussed more specifically below. Generally, however, it is noted that the activation and expulsion mechanisms may be entirely mechanical or involve a combination of mechanical and electronic components such as micro-mechanical pumps, heating elements, sensors, circuitry for controlling the rate and duration of the injection, as well as circuitry for wireless transmission to the external device.

Figure 2B:
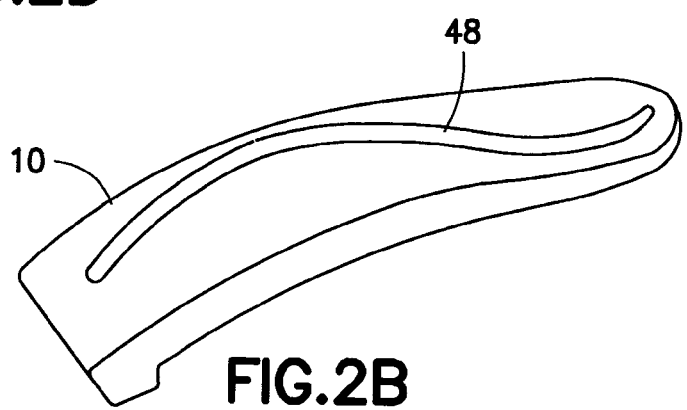
FIG. 2B is a photographic representation of the self-injection device of FIG. 1A in accordance with an embodiment of the present invention.
Figure 3A:
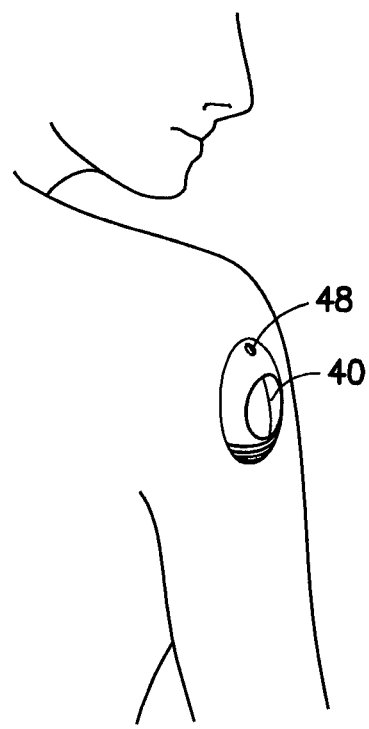
FIG. 3A is a perspective view of a self-injection device according to another embodiment of the present invention being worn by a patient.
Figure 3B:
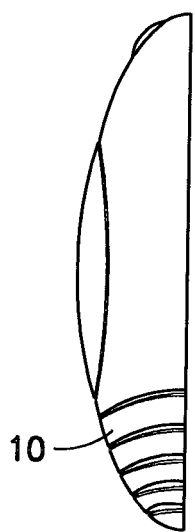
FIG. 3B is a side view of the self-injection device of FIG. 3A in accordance with an embodiment of the present invention.
Figure 3C:
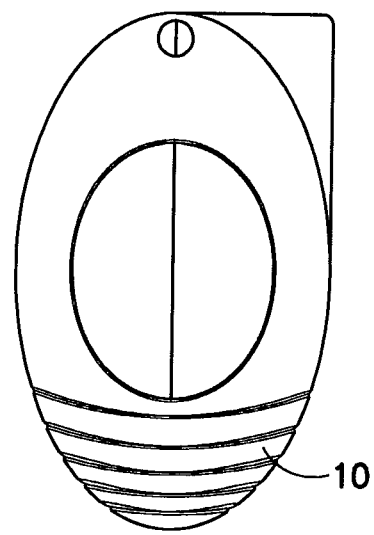
FIG. 3C is a top view of the self-injection device of FIG. 3A in accordance with an embodiment of the present invention.
Figure 3D:
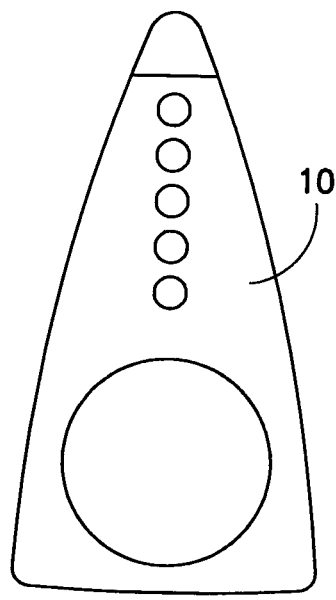
FIG. 3D is a top view of an activator for activating the self-injection device of FIG. 3A in accordance with an embodiment of the present invention.
Figure 3E:
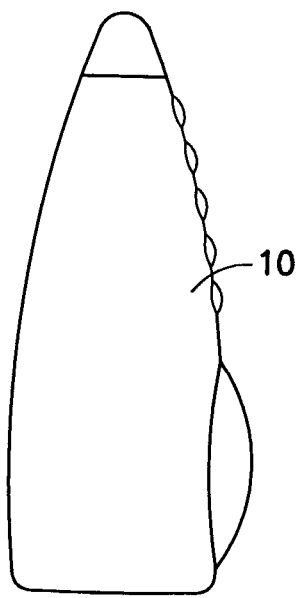
FIG. 3E is a side view of the activator of FIG. 3D in accordance with an embodiment of the present invention.
Figure 3G:
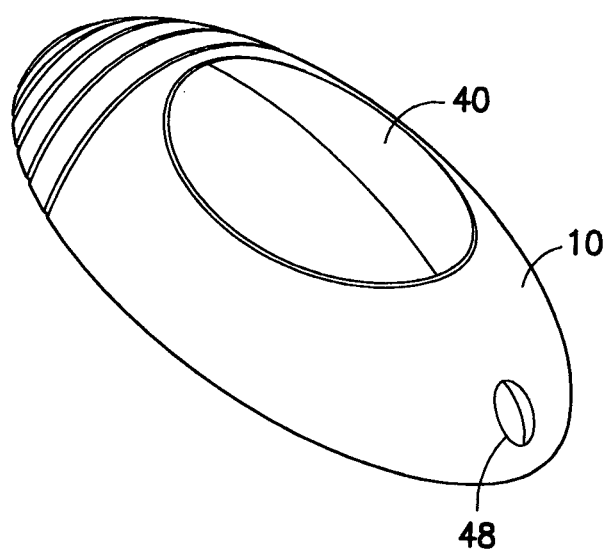
FIG. 3G is a perspective view of the self-injection device of FIG. 3A in accordance with an embodiment of the present invention.

In some embodiments, the injection may be substantially passive and unnoticeable to the user. In these configurations, the user is unable to gauge when the injection is completed. Therefore, according to one embodiment of the invention, the self-injection device further includes an indicator 48 (as shown in FIG. 2B) for alerting the user that the injection is complete. The indicator could be a structural component of the self-injection device itself such as a light emitting diode (LED) attached to the external housing which lights up when the injection is complete. Alternatively, a wireless signal could be sent to the user's external electronic device instructing the external electronic device to display a message that the injection is completed.

For embodiments of the self-injection device having electronic components for one or both of the activation or expulsion mechanisms, the self-injection device further includes a power supply, for example, a battery. A battery comprises one or more electrochemical cells that convert stored chemical energy into electrical energy. Generally, small sized electronic devices are powered by a button cell battery (i.e., a watch battery) or other similarly configured small single cell disposable battery. Button batteries are generally squat and cylindrical in shape with dimensions of about 5 mm to 12 mm in diameter and 1 mm to 6 mm in height. These batteries are usually disposable. Common anode materials are zinc or lithium. Common cathode materials are manganese dioxide, silver oxide, carbon monofluoride, cupric oxide, or oxygen from the air. Ultrathin flexible batteries are also known and may be adapted for use with the self-injection device. The ultrathin flexible batteries consist of anode, electrolyte, such as lithium phosphorus oxynitride, cathode, and current collector layers deposited on a substrate made of a flexible material.

Alternatively, a supercapacitor (e.g., an electronic double-layer capacitor (EDLC)) may be used as a power source. In contrast to a battery which is well suited for delivering a steady stream of power over a long period of time, a supercapacitor is well suited for a one-time delivery of power to a device. Notably, supercapacitors maintain a charge for longer time periods than a traditional battery meaning that the supercapacitor could be installed months or years before the device is used. Supercapacitors also have a faster discharge rate than traditional batteries making them well-suited for applications in which a single discharge of power for one purpose is required rather than a long term controlled release of power.

Another potential power source is a short burst of power provided wirelessly by an external device such as a smart phone. While the power provided from such a wireless signal is rather small, it would be sufficient to activate a triggering gate such as a thyristor. The activated trigger gate functions as an electrical switch which could be used to initiate the passive expulsion process. A configuration using a trigger gate would permit external activation without the added complexity of including a wireless transmitter on the injection device.

In a further non-limiting embodiment of the invention, the power source is the battery of a smartphone or a handheld electronic device. In this embodiment, an ultra-thin reservoir is embedded on the back-side of the plastic housing of the smartphone. The housing includes a plug (not shown) for connecting the port of the smartphone to the drug delivery device thereby providing sufficient electricity to power the actuation mechanisms such as the actuation mechanism depicted in FIGS. 9A and 9B. An additional advantage of having a connection between the smartphone and drug delivery device is that the smartphone can be used to provide a user with an alert when delivery of the drug is completed. Furthermore, the smartphone can be used to report that drug delivery or vaccine administration has been completed to an external source such as a computer server or website. The smartphone may also record and transmit other data regarding the injection such as the geographic location where the injection was performed and the time and date of the injection. This information can, in turn, be used by care givers, doctors, pharmaceutical companies, or third party payment organizations (e.g., insurance companies or public health services). In this embodiment, the fact that the reservoir and actuation mechanisms are miniaturized allows electronic components to be included in the drug delivery device without changing the overall appearance and form of the external housing to accommodate these additional electronic components.

With continued reference to FIGS. 5-7B, the expulsion mechanism 50 according to one non-limiting embodiment of the present invention is described. As shown in FIGS. 5 and 6A, a hemispherical reservoir 30 is carved from a substrate layer 32. When used to deliver a flu vaccine, for example, the reservoir 30 has a volume of about 100 µL. Needle 22 is placed at a bottom portion of the reservoir 30 establishing a fluid channel extending from the reservoir 30 through the substrate layer 32. A membrane layer 34 is deposited on top of the substrate layer 32 which encloses and isolates reservoir 30. Accordingly, the reservoir 30 is only accessible through the needle 22. The membrane 34 is, optionally, a layer of thin glass with a cross-sectional width of about 0.03 mm. An upper structural layer 36 is deposited above the membrane layer 34. The upper structural layer 36 is similar in size and composition to the substrate layer 32.

The upper structural layer 36 includes an expulsion reservoir 52 located directly above the fluid reservoir 30. The expulsion reservoir 52 is separated from the fluid reservoir 30 by the membrane 34. In one non-limiting embodiment of the expulsion mechanism 50, the expulsion reservoir 52 is filled with particles which swell when activated. As the particles increase in size, the volume of the expulsion reservoir 52 must increase to accommodate the increased volume of the larger particles. As a result, the particles exert a force on membrane layer 34 forcing the membrane layer 34 into space originally occupied by the fluid reservoir 30. As the particles continue to expand further reducing the volume of the fluid reservoir 30, the fluid is expelled from the reservoir 30 through the needle 22. Materials suitable for use as swellable particles include numerous cross-linked polymers such as poly acrylic acids, hydrolyzed products of starch-acrylic acid, vinyl acetate-acrylic acid ester copolymers, and hydrolyzed products of acrylonitriles. To fully expel liquid contained within reservoir 30, the particles must be capable of expanding by a factor of about 4 or more.

With continued reference to FIGS. 5-7B, the expulsion mechanism 50 further includes an activation reservoir 54 also carved from the upper structural layer 36. The activation reservoir 54 contains the fluid for expanding the particles contained in the expulsion reservoir 52. The activation reservoir 54 is the smallest of the three reservoirs. Necessarily, the activation reservoir 54 must contain sufficient fluid to permit the particles to expand sufficiently to drive all fluid from the fluid reservoir 30. The choice of activation fluid is dependent on the type of expandable particles used. For the hydrophilic ionic particles described above, the activation reservoir 54 contains water. A channel 56 connecting the activation reservoir 54 and expulsion reservoir 52 is cut within the upper structural layer 36. A seal (not shown) prevents the fluid in the activation reservoir 54 from flowing toward the expulsion reservoir 52 until the user is ready to begin the injection (i.e., the user engages the activator or initiates an activation activity).

In one embodiment of the delivery portion 20, the upper layer 36, including the activation reservoir 54 and expulsion reservoir 52, is positioned beside, rather than on top of, the substrate layer 32. Side by side arrangement of the substrate layer 32 and upper layer 36 provides a drug delivery portion 20 with a substantially thinner profile. The thinner drug delivery portion 20 fits more easily into certain external housing designs. Accordingly, the range of options for types of external housings, and for the aesthetic and human factors that the housings address, is substantially increased.

In one embodiment, the activation activity is simply manually and directly ejecting the activation fluid (e.g., water) from the activation reservoir 54. For example, a user may press a button located on the external housing which deforms the activation reservoir 54 or, alternatively, drives a plunger through the activation reservoir 54. The applied force breaks the seal allowing the water to flow through channel 56 toward the expulsion reservoir 52. In addition to the manual expulsion force, any of the other activation means described above, including wireless activation, can be adapted for use with this embodiment of the self-injection device. For example, the activation reservoir may contain a mechanical gate which opens in response to an electrical signal. The signal could be sent from an activator located on the self-injection device itself or which is sent from an external electronic device. Alternatively, the activation reservoir 54 could be in connection with a micro-pump which begins to operate, expelling the activation fluid from the reservoir.

Figure 7A:
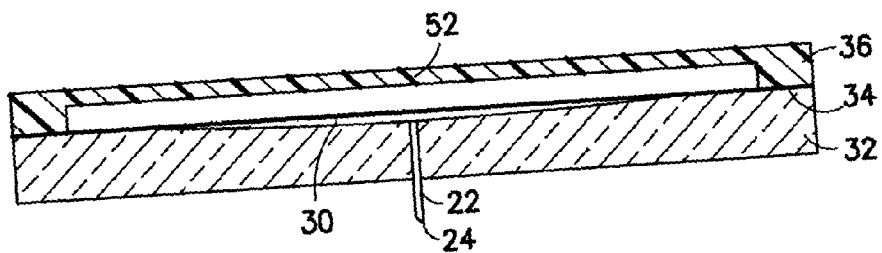
FIG. 7A is a side cross-sectional view of the drug delivery portion of FIG. 6A in accordance with an embodiment of the present invention.
Figure 7B:
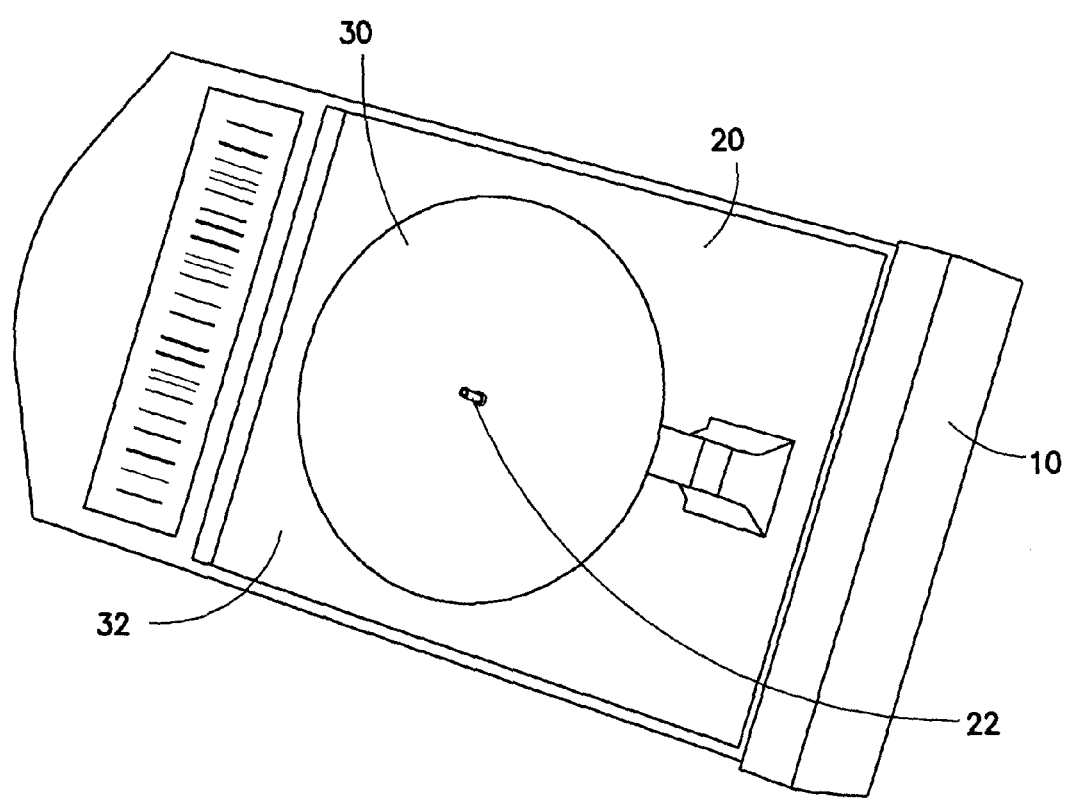
FIG. 7B is a perspective view of the drug delivery portion of FIG. 7A enclosed within the housing in accordance with an embodiment of the present invention.

With reference now to FIG. 7B, the embodiment of the drug delivery portion 20 is shown enclosed within the housing 10. The R value for the embodiment of the invention depicted in FIG. 7B is lower than 0.3.

Figure 8:
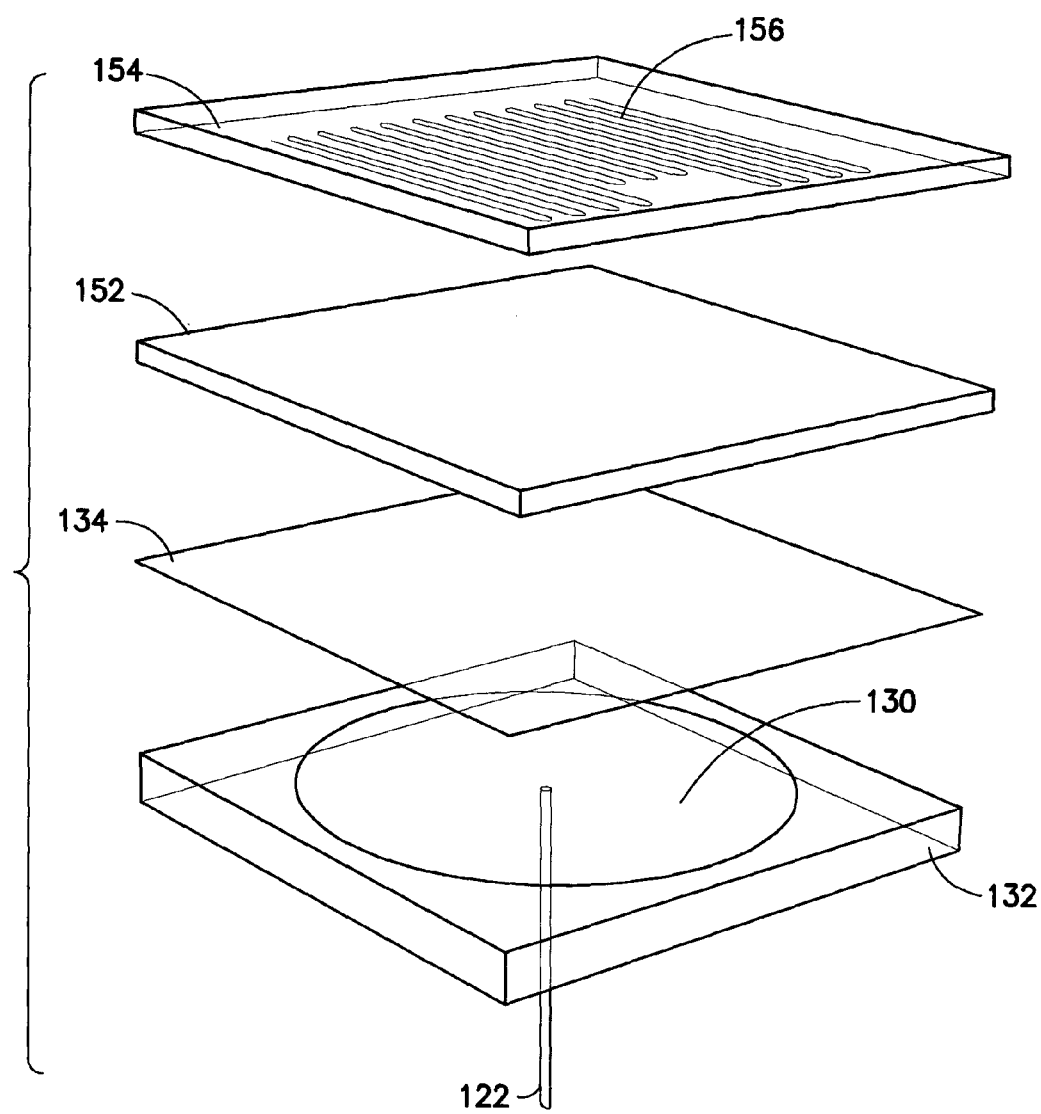
FIG. 8 is an exploded perspective view of a drug delivery portion of the self-injection device of FIG. 7A in accordance with an embodiment of the present invention.

With reference now to FIG. 8, a second non-limiting embodiment of the drug delivery portion of the self-injection device is depicted. The two bottom most layers (e.g., a substrate layer 132 and a membrane layer 134) and a needle 122 of this embodiment are generally identical in size and composition to the corresponding structures in the embodiment of the device depicted in FIGS. 5-7B described above. As in the previously described embodiment, the reservoir 130 is adapted to contain about 100 µL of fluid which is sufficient for a single dose of flu vaccine for intradermal injection. The activation reservoir 54 of the embodiment of FIGS. 5-7B is replaced by a heat activated expandable layer 152. In one embodiment, the expandable layer 152 comprises an elastomer layer with embedded expandable microspheres, such as those provided under the trade name EXPANCEL™. EXPANCEL™ spheres have a volume expansion of about 2.7 times at 80 degrees Celsius. In another embodiment, the expandable layer is paraffin oil.

The activation component of the embodiment of the device depicted in FIG. 8 is a heating layer 154 deposited above the expandable layer 152. In one embodiment, the heating layer 154 is a glass layer enclosing a thin film 156 having resistance such that the film heats up when exposed to electrical current. The film 156 will need to be connected to a power source (not shown) to provide the electrical current. As previously described, the power source can be any number of power providing devices including batteries, supercapacitors, or power provided through the data/power port or wirelessly from an external device.

In use, the delivery portion depicted in FIG. 8 is activated by any of the active and unexpected activation means described previously. In response to the activation activity, an electrical connection is established between the power source and the resistive heating film 156 contained within the heating layer 154 permitting the flow of electrical current therebetween. The electrical connection could be established by activating an electrical switch or other electrical component such as a trigger gate, transistor, or thyristor. In response to heat from the film 156, the expandable layer 152 expands exerting a downward force on the membrane layer 134. The movement of the membrane layer 134 reduces the volume of the fluid containing reservoir 130 thereby expelling the fluid contained therein from the reservoir 130 through the needle 122.

Figure 9A:
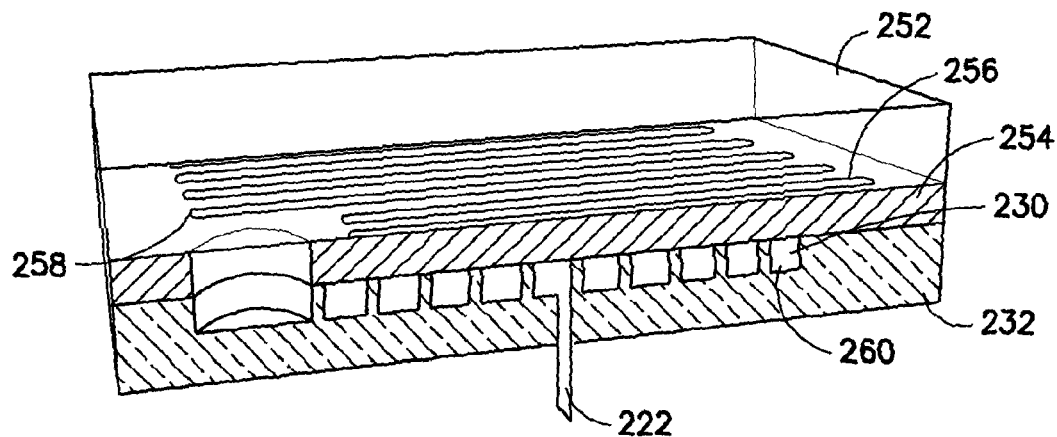
FIG. 9A is a perspective view of the drug delivery portion of the self-injection device in accordance with an embodiment of the present invention.
Figure 9B:
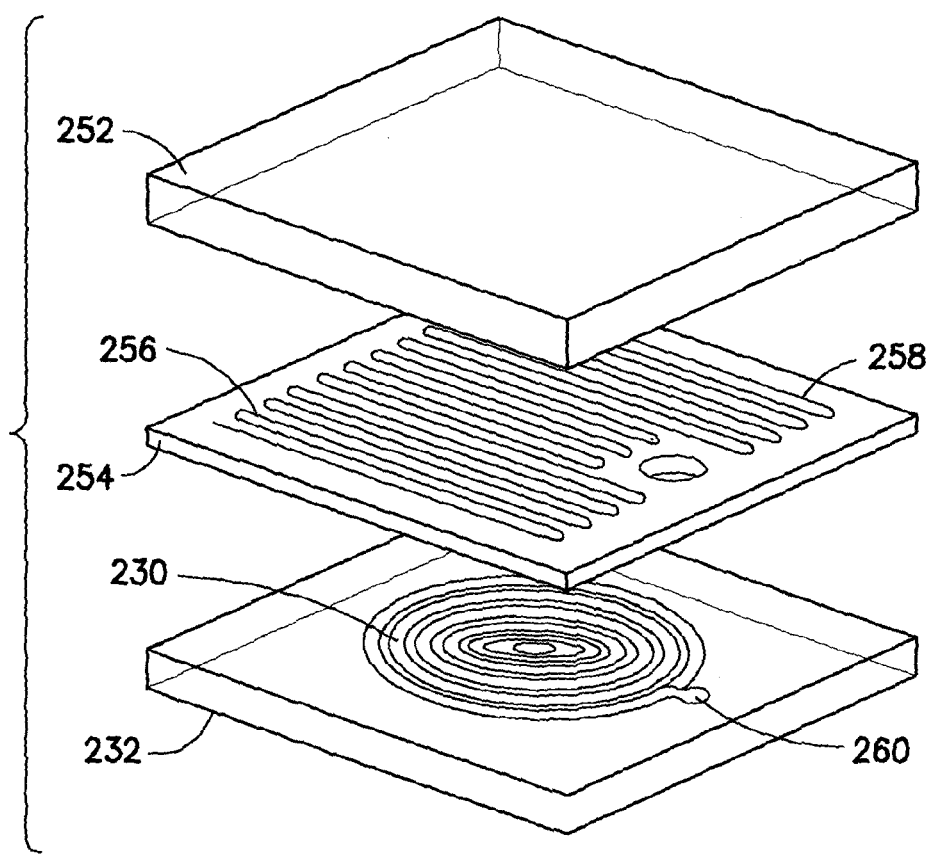
FIG. 9B is an exploded view of the drug delivery portion of FIG. 9A in accordance with an embodiment of the present invention.
Figure 9C:
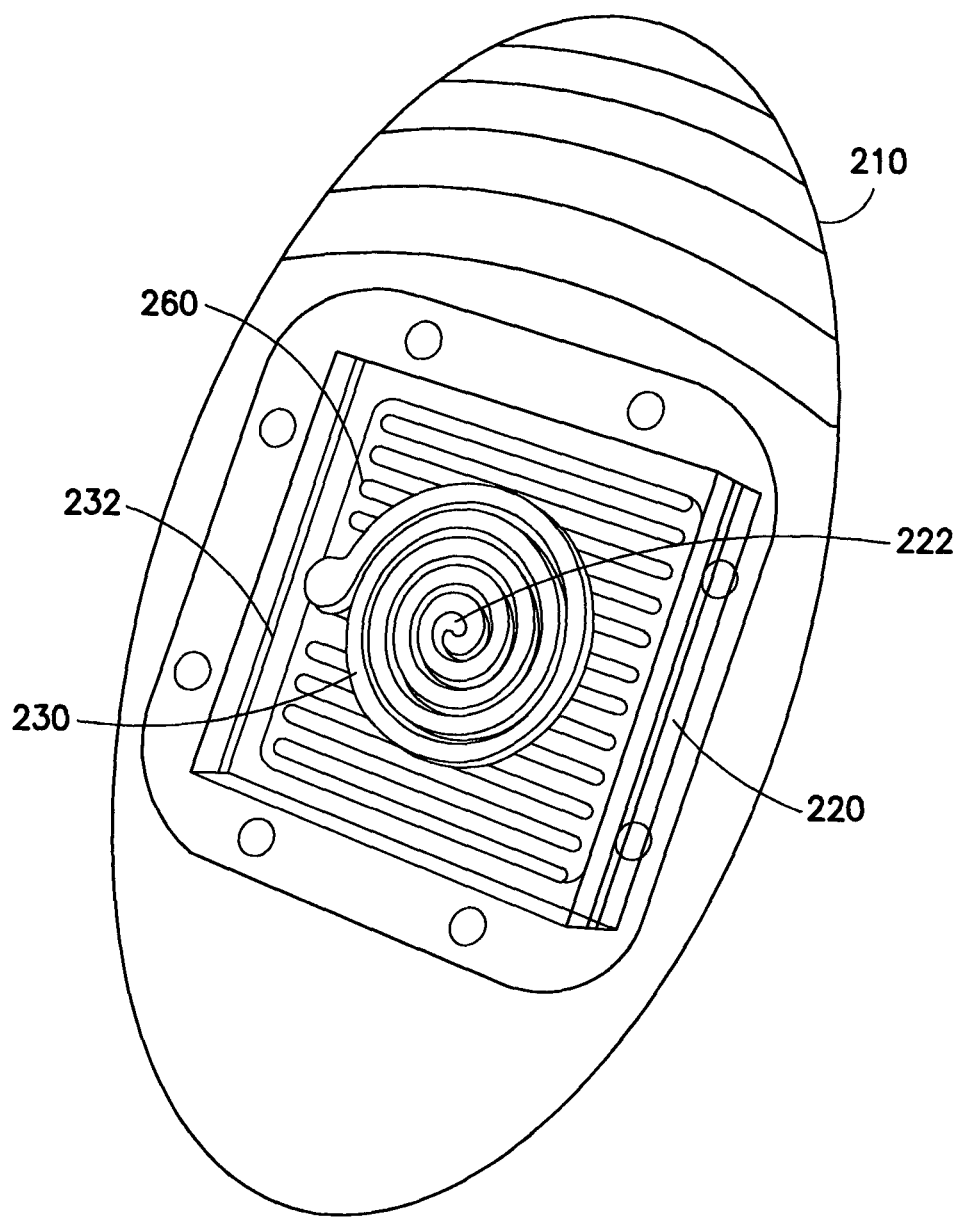
FIG. 9C is a view of the drug delivery portion of FIG. 9A having a translucent outer layer so that interior components are visible in accordance with an embodiment of the present invention.

With reference now to FIGS. 9A-9C, another embodiment of a drug delivery portion 220 of the self-injection device having a labyrinth shaped reservoir 230 is depicted. As in the embodiments of the delivery portion described above and depicted in FIGS. 5-8, the present embodiment includes a substrate layer 232 and needle 222. As with previously described embodiments, the substrate can be formed from any suitable material having the required structural stability and approved to contain a therapeutic agent for injection including glass and medical grade polymers. A portion of the substrate layer 232 is removed by a suitable process such as acid etching to create the labyrinth shaped reservoir 230. The needle 222 is placed in the substrate layer 232 at the center of the labyrinth reservoir 230. The fluid to be delivered to the user is contained within the labyrinth reservoir 230. The fluid is expelled from the reservoir 230 by a material which is solid at room temperature but which becomes flowable when exposed to heat. An exemplary material is paraffin wax. A heating layer 254 is deposited above the reservoir containing substrate layer 232. The heating layer 254 is similar in composition and function to the heating layer in FIG. 8. Specifically, the heating layer 254 contains a thin resistive film or resistance coils 256 which become hot when an electric current is passed through them. The electric current is provided by a power source such as one of the power sources described above. An expulsion reservoir 252 containing the flowable material (e.g., paraffin wax) is deposited above the heating layer 254. The expulsion reservoir 252 includes an outlet channel 258 for establishing a fluid connection between the expulsion reservoir 252 and fluid labyrinth reservoir 230. The outlet channel 258 opens to the most distal portion (i.e., the start) of the labyrinth reservoir 230.

When the heating layer 254 is activated, the material contained in the expulsion reservoir 252 softens and becomes flowable causing the material to flow downward through the outlet channel 258. The flowable material enters the labyrinth reservoir 230 at its most distal portion. As the flowable material continues to enter the labyrinth reservoir 230, it exerts force on a stopper 260 thereby forcing the stopper 260 to advance through the labyrinth reservoir 230. The stopper 260 can be a wide variety of structures or materials which maintain separation between the flowable material and fluid therapeutic agent. Notably, the material should not degrade in response to heat or adversely interact with either the fluid contained in the reservoir or the flowable material. In one non-limiting embodiment, the stopper 260 is a small amount of silicone oil. As the stopper 260 advances through the reservoir 230, fluid contained therein is forced toward the center of the reservoir 230. The fluid exits the reservoir through the needle 222 located in the reservoir 230 center for delivery to the user.

With reference now to FIG. 9C, the embodiment of the drug delivery portion 220 is shown enclosed within a housing 210. The R value for the embodiment of the invention depicted in FIG. 9C is approximately 0.3.

It is understood, however, that many other expulsion mechanisms are possible for drug delivery devices within the scope of the present invention. For example, an expulsion mechanism which deforms a diagram (such as membrane layer (34, 134)) to expel fluid from the reservoir could rely on piezoelectric actuation, electrostatic actuation, electromagnetic or magnetic actuation, as well as by thermal actuation and actuation by expandable microspheres as described above. Pneumatic actuation by releasing compressed gas to expel fluid from the reservoir is also possible. Micro-pumping techniques using rotary pumps manufactured by micromachining techniques currently used in the microprocessor industry may also be used to draw fluid from the reservoir. Alternatively, electro and magneto-kinetic (rather than mechanical) expulsion methods are also possible. Electrokinetic pumps utilize an electric field to drive ions within a pumping channel; magneto-kinetic pumps typically utilize Lorentz forces on the bulk fluid to drive the microchannel flow.

The drug delivery portions of the self-injection device described above are designed to hold small volumes of fluid, such as a single dose of an intra-dermal injection of flu vaccine (0.1 mL). Other applications requiring small volumes of injection include intra-dermal injections of other vaccines (such as HPV), de-sensitization for allergies, and emergency pain reliever (e.g., lidocaine). However, the drug delivery device of the present invention may also be applied to larger volume injections. The above described embodiments of the drug delivery portions can be used for reservoir sizes up to about 0.5 mL. With slight modification to the design, the reservoir may be further adapted to contain a fluid volume in the range of 100 mL. One configuration capable of containing greater volumes of fluid is obtained by stacking smaller volume drug delivery chips on top of one another to create a composite chip having a greater total reservoir volume.

In addition, volumes larger than 0.1 mL can also be obtained through use of ultra-thin reservoirs with an extended surface area. For example, a MEMS chip or an assembly of connected MEMS chips occupying a surface area equivalent to that of commercially available smartphones or other handheld electronic devices, and having a thickness of 200 μm, could contain up to 2 mL of liquid.

While it is understood that as the injection volume increases the volume of the functional portion of the device ($V_{Functional\_part}$) will increase proportionally, the mere fact that the actuation mechanism is embedded within the drug delivery portion of the device itself means that the functional volume will always be smaller than a classical syringe configured for the same injection volume. Specifically, a standard syringe has a plunger rod, which essentially doubles the volume of the functional portion of the injection device. Therefore, drug delivery devices of the present invention systematically reduce the R parameter by a factor of 2 compared to a standard syringe regardless of the volume of fluid to be injected.

Figure 10:
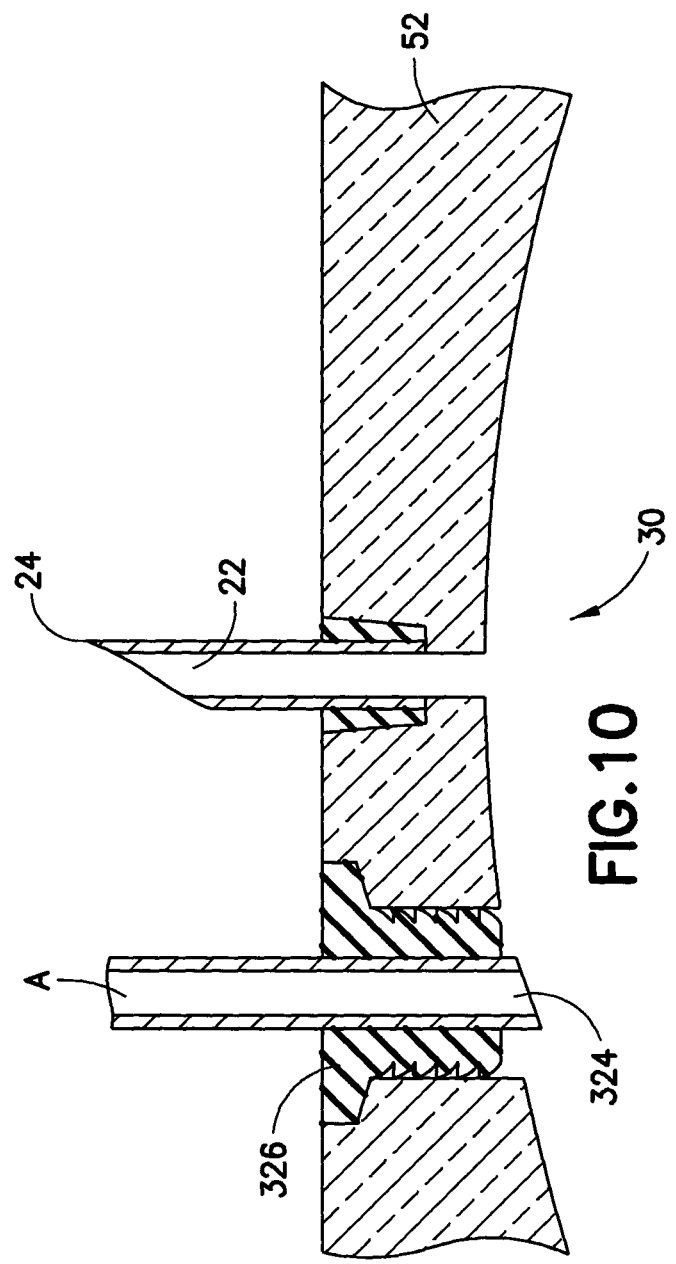
FIG. 10 is an enlarged partial cross-sectional front view of the substrate layer and reservoir of the drug delivery portion in accordance with an embodiment of the present invention.
Figure 11A:
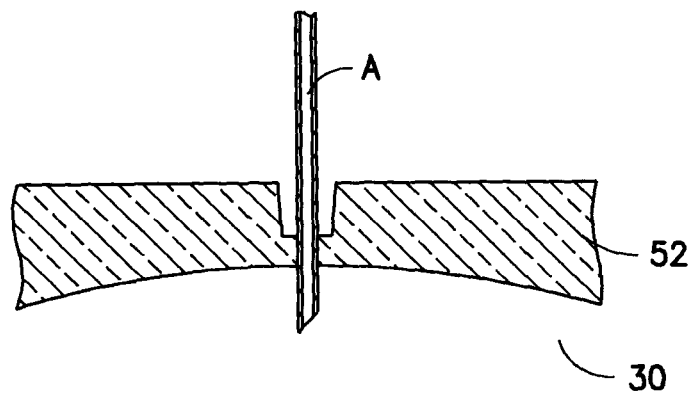
FIG. 11A is an enlarged cross-sectional front view of a drug delivery portion in accordance with the present invention.
Figure 11B:
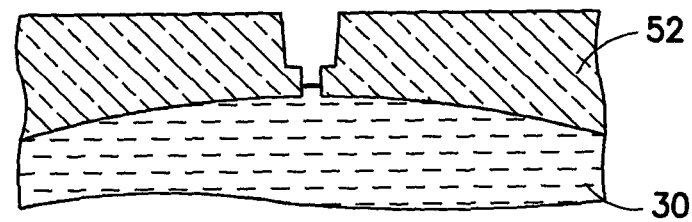
FIG. 11B is an enlarged cross-sectional front view of a drug delivery portion in accordance with the present invention.
Figure 11C:
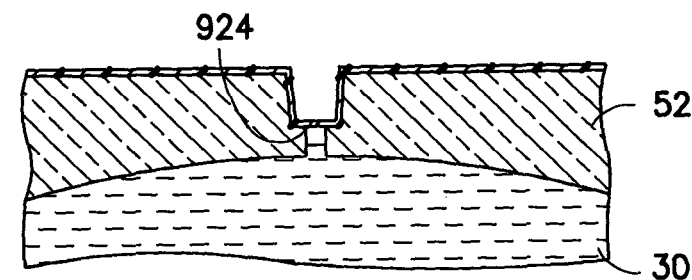
FIG. 11C is an enlarged cross-sectional front view of a drug delivery portion in accordance with the present invention.
Figure 11D:
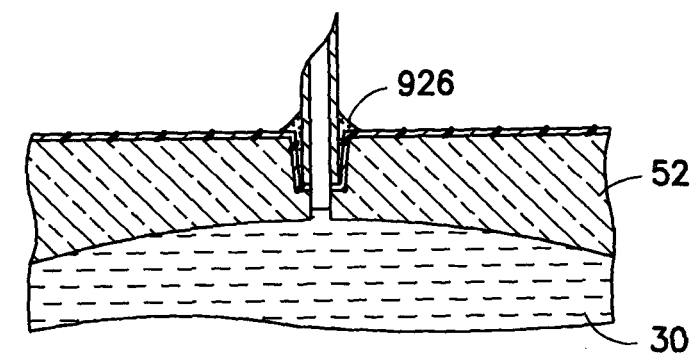
FIG. 11D is an enlarged cross-sectional front view of a drug delivery portion in accordance with the present invention.

With reference now to FIGS. 10-11D, an expanded view of the reservoir 30 of the drug delivery portion 20 is depicted for the purpose of explaining how the reservoir is filled prior to use. The filling methods can be used with any of the embodiments of the device described above. As shown in the embodiment depicted in FIG. 10, the reservoir 30 includes a second fluid channel 324 formed in the substrate layer 32 for permitting access to the reservoir 30. The channel 324 is closed by an elastomeric plug 326. The plug 326 is adapted to be pierced by a filling needle from a filling machine A. The filling needle A is pushed through the plug 326 thereby providing a second source of access to the reservoir 30. Fluid is then pushed into the reservoir 30 through the filling needle A. Air is vented from the reservoir through the needle 22. The filling needle A is then removed from the reservoir 30 by pulling away from the deformable plug 326. Once the filling needle A is removed from the plug 326, the flexible elastomeric material reseals thereby preventing fluid from leaking from the reservoir 30.

Alternatively, as depicted in FIGS. 11A-11D, the reservoir 30 is filled by a vacuum suction method. According to the vacuum suction method, the self-injection device is placed in a vacuum chamber to evacuate air from the reservoir 30. Once air is evacuated from the chamber, a needle A from a filling machine can be injected to the reservoir 30 and fluid injected through the needle to the reservoir 30. Notably, since the reservoir was evacuated by a vacuum, venting is not required since no air is contained within the reservoir. Additionally, as a result of the difference in pressure between the reservoir and the filling machine, the fluid is drawn (i.e., sucked) into the reservoir 30 meaning that no pumping is required to introduce the fluid to the reservoir. Once the fluid is injected to the reservoir, the filling needle A is removed and a fill cap 424 is placed over the injection site. Exemplary cap materials include a thin hydrophobic film or a UV cured polymer. Once the fill cap 424 is in place, the needle 22 is inserted in place at the base of the reservoir 30. The needle 22 is anchored to the substrate layer 32 by an adhesive 426 such as glue.

A further aspect of the present invention is drawn to a method of manufacturing the miniaturized injection system, installing the injection system within a suitable housing, and filling the device with a therapeutic agent such as a vaccine or drug. According to one non-limiting embodiment, the manufacturing method is based largely on manufacturing processes which were developed for use in the semiconductor and electronics industry and are commonly used to make integrated circuits, electronic packages, and other microelectronic or micro-electric-mechanical devices. Other techniques used in the invented method of manufacture are adapted from the field of micromachining. However, the method of manufacture described below is intended only as a non-limiting exemplary method for manufacturing the self-injection device of FIGS. 1A-9C. It is understood that the self-injection device of the present invention can be formed in numerous other ways which do not rely on semiconductor manufacturing principles and, nevertheless, fall within the scope of the invented device and method.

It is desired that the manufacturing method permit large scale batch manufacturing of the injection device to reduce cost, as well as to permit filling of the reservoirs at a rate compatible with market needs. Batch production is a manufacturing technique in which numerous articles are prepared in parallel rather than in an assembly line fashion in which only a single device is acted on at a time. It is envisioned that batch manufacturing will increase production rate for the injection device, thereby reducing costs per device.

According to the inventive method of manufacture, a substrate is provided. Optionally, the substrate is a thin glass layer produced by any acceptable method including float processing and fusion processing (overflow down draw process). The float process (also known as the Pilkington process) involves floating molten glass on a bed of molten metal to create a sheet of uniform thickness. In the fusion production method, molten glass is permitted to flow down opposite sides of a tapered trough forming two thin molten streams. The two glass streams rejoin or fuse at the base of the trough forming a single sheet having excellent uniformity of depth and composition. The fusion process is a technique for producing flat glass often used in the manufacture of flat panel displays. Advantageously, the technique produces glass with a more pristine surface, as the surface is not touched by molten metal. Glass produced by this technique is widely commercially available and is produced by companies including Schott, Corning, Samsung, and Nippon Electronic Glass. Alternatively, substrate materials including medical grade polymers and silicone could also be used within the scope of the invented method.

The substrate is provided as a large sheet on which numerous drug delivery devices will be formed. Recent advances in glass fabrication techniques (especially in the field of flat glass for flat panel displays) have greatly increased the size of flat glass panels which are commercially available. Currently, panels encompassing several square meters are commercially available. In one preferred embodiment of the present method, 8×8- to 17×17-inch square glass wafers, which can be manufactured to contain between about 40 and 200 delivery devices, are used as a substrate material.

Once the substrate is provided, the reservoirs or cavities are formed on the substrate. A person of skill in the art will recognize that many techniques exist for forming a depression in a glass substrate which will serve as a fluid containing cavity. According to one embodiment, the cavity is formed by wet etching in which a strong acid (e.g., hydrofluoric acid) is exposed to unprotected portions of the glass surface. The depth of the etched cavity can be approximately controlled by estimating the decomposition rate of the substrate based on the composition of the reagent. It is understood that some reagents are isotropic in that they cause the substrate to degrade at an equal rate in all directions forming a hemispherical depression. Anisotropic reagents only degrade the substrate in the vertical (depth) direction resulting in depressions that are essentially rectangular in shape. It is understood that other etching techniques may also be used to form the reservoir including plasma (dry) etching, in which a high-speed stream of plasma (e.g., glow discharge particles) on an appropriate gas mixture is shot at the sample to form the depression. It is also possible to attach a pre-formed reservoir to the substrate rather than forming the reservoir within the substrate. As described above, the dimensions of the cavity or reservoir should be as small as possible, but sufficient to hold a single dose of drug or vaccine. According to one embodiment of the invention, adopted for use with flu vaccine, the reservoir is 100 µL.

Once the reservoir is formed, the microneedle is placed in the reservoir. As described above, the microneedle is a hollow needle formed from metal or other suitably strong material. The needle is placed using an automated "pick and place" machine similar to machines used for placing transistors on a circuit board. It is further envisioned, according to one embodiment, that multiple needles will be placed in separate reservoirs of the wafer at the same time. In this way, the time required to produce each delivery device and reservoir on the substrate can be significantly reduced. Optionally, the microneedle is anchored to the substrate using an adhesive material such as glue. In addition, the microneedle structure may further include a stopper material to prevent the fluid from being expelled from the reservoir prematurely. For example, a thin breakable film or membrane may be included within the needle lumen. The film or membrane should be sufficiently strong and stable to prevent the fluid from escaping from the reservoir. However, once the injection device is activated, and the expulsion mechanism begins to reduce the volume of the reservoir chamber, the force applied to the thin membrane is increased. In response to this increase in force, the film or membrane breaks allowing fluid to pass through the needle for delivery to the user.

Upper layers, including one or more of a thin glass membrane layer to enclose and separate the fluid reservoir from the rest of the delivery device, upper structural layers having similar dimensions and composition to the substrate layer, a drive mechanism, and an activator may be deposited above the substrate layer and fluid containing reservoir. These upper layers and mechanical structures are placed using similar micro-manufacturing techniques to the method for placing the microneedle within the reservoir. As described above, it is desirable to place components according to a batch protection method in which components for multiple injection devices are placed simultaneously.

Once the layers and components for each reservoir are assembled on the wafer substrate, the wafer is divided into individual injection devices. The wafer may be divided by any suitable process capable of making rapid exact and small cuts through the wafer. One cutting process well suited for this application is laser cutting. Mechanical and plasma cutting techniques can also be adapted for dividing the larger wafer into individual injection devices.

At some point during the manufacture or distribution process, the injection devices are filled with the vaccine or drug to be delivered to the user. One possibility is that the reservoirs can be filled during the manufacturing process before the larger wafers are separated into individual devices. In this case, the injection devices are sold to consumers as pre-filled injection devices. Alternatively, the injection devices could be filled later such as after they are purchased by and shipped to a pharmaceutical company or pharmacy. In either case, filling can be accomplished by several approaches. The examples provided herein are but two of the multiple available methods for filling an injection device. One of skill in the art will appreciate that other filling methods are similarly available.

In one filling method, the injection device includes a second fluid channel formed in the substrate for permitting access to the reservoir. The channel is closed by an elastomeric plug. The plug is adapted to be pierced by a filling needle. The filling needle is pushed through the plug thereby providing a second source of access to the reservoir. Fluid is then pushed into the reservoir through the filling needle. Air is vented from the reservoir through the microneedle (injection needle). The filling needle is then remove from the reservoir by pulling away from the elastomeric plug. Once the filling needle is removed from the plug, the flexible elastomeric material reseals thereby preventing fluid from leaking from the reservoir Alternatively, the reservoir is filled by a vacuum suction method. According to the vacuum suction method, the injection device is placed in a vacuum chamber to evacuate air from the reservoir cavity. Once air is evacuated from the chamber, a needle from a filling machine can be injected to the reservoir and fluid injected through the needle to the reservoir. Notably, since the reservoir was evacuated by a vacuum, venting is not required since no air is contained within the reservoir. Additionally, as a result of the difference in pressure between the reservoir and the filling machine, the fluid is drawn (i.e., sucked) into the reservoir meaning that no pumping is required to introduce the fluid to the reservoir. Once the fluid is injected to the reservoir, the filling needle is removed and a film cap is placed over the injection site. Exemplary cap materials include a thin hydrophobic film or a UV cured polymer.

According to one embodiment of the vacuum suction filling method, the microneedle is installed after the reservoir has been filled. After filling, the microneedle is inserted into the reservoir through the film cap. The film cap then serves as a breakable septum for maintaining the fluid in the reservoir until activation occurs. Once the device is activated, the increased force against the cap or septum causes the cap to break and allows fluid to flow from the reservoir through the microneedle.

Once the injection device is fully assembled and filled, the injection portion of the device is placed in a housing. As stated above, it is necessary that the housing be visually appealing to users to encourage them to participate in optional medical procedures such as voluntary immunizations. The injection device is placed in the housing a dedicated "pick and place" machine adapted for that purpose.

When considering the method of manufacture for the self-injection device, it is understood that multiple steps which require microfabrication machines could be performed together. For example, the steps of dividing the devices by cutting the wafer and placing the individual wafers in housings could be performed simultaneously by the same "pick and place" type machine.

According to another non-limiting embodiment of the present invention, the miniaturized injection system is formed using Rapid Prototyping and 3D Printing technologies. 3D Printing machines are commercially available from various sources including Object Technologies, LLC located in Forest Hills, N.Y. Rapid Prototyping is generally defined as a group of techniques used to created a three dimensional model based on computer aided design (CAD) data. Construction of the object is done using 3D Printing technology. A 3D Printing machine uses an additive process in which an object is created by laying down successive layers of material on top of one another to form a 3D structure based on data from a CAD drawing. In one non-limiting embodiment of the invention, each layer is approximately 16 µm thick. In the present invention, the material may be a medical grade polymer resin. Alternatively, 3D Printing techniques using metal alloys are also known in the art. The miniaturized injection system including substrate layer, the one or more reservoirs, and upper layers can be formed using 3D Printing. The injection needle can be added after 3D Printing is complete according to the pick and place method described above. The reservoir can be filled according to any of the methods described above.

Additional manufacturing concerns for the injection devices arise from the fact that these devices are being used for medical purposes and, accordingly, must follow FDA protocols for the manufacture of medical devices.

Example

Five device designs were presented to a panel of 20 people as device options for performing a hypothetical act of self-vaccination. This hypothetical act was chosen because it is a practice that is traditionally performed by a healthcare professional. In each case, the panelists were given instructions on how to use the device. Device 1 was the delivery device resembling a bracelet, as described above and shown in FIGS. 2A-2D. Device 1 is gently applied to the forearm of the user and includes an end-of-dose indicator. Device 1 was intended to suggest an ornamental and innocuous object, associated with a soft and comforting gesture to be used properly. The R value of the Device 1 is about 0.3 and the AR value is 3.525. The $R^1$ value is 3.80 (380%). It was the preferred design, chosen by 50% of the panelists.

Device 2 was the delivery device resembling a small pod or button, as described above and shown in FIGS. 3A-3G. Device 2 is applied to the arm, and remotely connected to a smartphone for activation and follow-up of the injection. Device 2 was intended to suggest accuracy of the administration protocol via an activator that is familiar and associates the administration with the sphere of individual health control. The R value of Device 2 is about 0.3 and the AR value is 1.564. The R' value is 1.69 (169%). It was chosen as the preferred design by 25% of panelists.

Device 3 was the delivery device resembling a watch, as described above and shown in FIGS. 4A-4B. Device 3 can be plugged onto a traditional watch to facilitate positioning along the arm. Activation is again purely manual, and the device includes an end-of-dose indicator. Device 3 was meant to associate the administration protocol with a very familiar and low tech object which is frequently worn. The R value of the Device 3 is about 0.4 and the AR value is 1.205. The R' value is 1.30 (130%). This device was chosen by 15% of panelists.

Device 4 is a small delivery device, which is pressed on the forearm and described above with reference to the "Second Conventional Micro-Infusor". Device 4 contains a small glass barrel which is visible, and which moves downward as the injection proceeds. Absence of movement reveals the end of the dose. The R value is approximately 0.38 and the AR value is 1.414. The $R^1$ value is 100%. This device was chosen by 10% of panelists.

Device 5 is a conventional micro-infusor, which is a patch-like device that is applied and glued to the arm, before deploying the activating button, described above with reference to the "Conventional mirco-infusor". A shape appears on the top of the device when the injection is done. The R value is approximately 0.92 and the AR value is 1.447. The $R^1$ value is 96%. This device was chosen by 0% of the panelists. It is noted, however, that the dimensions of the micro-infuser housing cannot be substantially reduced without limiting the drug delivery capability of the device. Specifically, the volume of the housing cannot be reduced without contacting pipes or channels used to direct fluid from the micro-infuser reservoir to the patient. Thus, since the actual volume of the micro-infuser is very close to the minimal possible volume, according to the second method of calculating R described above, the R value of a micro-infuser is near 1.

None of these devices had the shape or were reminiscent of a syringe. Devices 4 and 5, however, are true delivery device prototypes that were conceived on the basis of the usual design rules, i.e., building around the filling constraints of the pharma industry.

Upon interviewing the panelists, it appeared clearly that their choice was mainly driven by the non-medical aspect of the device. Specifically, participants noted that the device they chose felt as if it had been customized for them. It is noted however, that it was never suggested to participants that certain devices were designed to appeal to certain groups of people.

This study shows that the non-functional part of the device has a considerable importance on a user's perception (i.e., confidence) about performing the injection. Therefore, it is believed that a better acceptance of injections in general can be obtained by reversing the design protocol of drug delivery devices. Specifically, it is shown that by starting from the human factors and, thereby, reducing the R (minimalization) value and increasing $R^1$ value (defining the similarity or lack of similarity in shape of the functional and nonfunctional elements) of the device, individuals are more accepting of performing self-injection. Further, such shapes can only be used to create delivery systems if the functional part is miniaturized compared to the existing functional delivery mechanisms.

What is claimed is:

1. A self-injection device with a miniaturized drug delivery component, the device comprising a housing having an interior volume consisting of a functional portion and a non-functional portion, the functional portion comprising:
   a substrate having a depression or cavity extending inwardly from a surface thereof, the depression or cavity defining a reservoir containing a single dose of a fluid to be delivered to a user;
   a microneedle mounted to the substrate in fluid communication with the reservoir and extendable through the housing; and
   a drive mechanism in communication with the substrate for expelling the fluid from the reservoir through the microneedle,
   wherein a volume of the functional portion is less than 40% of the interior volume of the housing.

2. The self-injection device of claim 1, wherein the volume of the functional portion is less than 30% of the interior volume of the housing.

3. The self-injection device of claim 1, wherein the volume of the functional portion is less than 20% of the interior volume of the housing.

4. The self-injection device of claim 1, wherein the microneedle is configured for intradermal injection.

5. The self-injection device of claim 4, wherein the microneedle is extendable from the housing a distance of between 1 mm and 2 mm.

6. The self-injection device of claim 1, wherein the reservoir contains at least one of a vaccine, a medicament, and a therapeutic agent.

7. The self-injection device of claim 1, wherein the drive mechanism expels fluid from the reservoir as a single continuous dose delivered at a clinically reasonable rate, and wherein the clinically reasonable rate is a total delivery time of no longer than 10 seconds.

8. The self-injection device of claim 1, wherein the functional portion further comprises an activator for engaging the drive mechanism, wherein the activator comprises a wireless receiver associated with the drive mechanism, and wherein the activator is configured to engage the drive mechanism when an activation instruction is received by the wireless receiver from an external control device.

9. The self-injection device of claim 8, wherein once engaged by the activator, the drive mechanism passively expels fluid from the reservoir.

10. The self-injection device of claim 1, wherein the functional portion further comprises an indicator which alerts the user when the fluid has been substantially expelled from the reservoir.

11. The self-injection device of claim 1, further comprising a wireless transmitter, wherein the wireless transmitter is configured to transmit an alert to an external control device when the fluid has been substantially expelled from the reservoir.

12. The self-injection device of claim 1, wherein an aspect ratio (AR) of the functional portion is defined by the equation $$AR = \frac{L3}{\sqrt{L1^2 + L2^2}},$$

wherein L1, L2, and L3 are lengths of dimensions of a smallest parallelepiped which encloses the functional portion, with $L1 \leq L2 \leq L3$,
   wherein an aspect ratio (AR) of the interior volume of the housing is defined by the equation $$AR = \frac{L3}{\sqrt{L1^2 + L2^2}},$$

wherein L1, L2, and L3 are lengths of dimensions of a smallest parallelepiped which encloses the interior volume of the housing, with $L1 \leq L2 \leq L3$, and
   wherein the ratio between the aspect ratio of the interior volume of the housing and the aspect ratio of the functional portion is at least 100%.

13. The self-injection device of claim 1, wherein the ratio between the aspect ratio of the interior volume of the housing and the aspect ratio of the functional portion is greater than 125%.

14. The self-injection device of claim 1, wherein the drive mechanism comprises a plurality of expandable members connected to the reservoir, and wherein when activated, the expandable members expand to expel fluid from the reservoir.

15. The self-injection device of claim 14, wherein the expandable members comprise hydrophilic ionic particles, which expand when exposed to water, or heat activated expandable cells.

16. The device of claim 14, wherein the drive mechanism further comprises an activation reservoir containing an activation fluid capable of activating the expandable members, and wherein upon activation of the self-injection device, the activation fluid is forced from the activation reservoir to the expandable members to cause expansion of the expandable members.

17. The device of claim 1, wherein the reservoir comprises a labyrinth shaped reservoir containing a substance capable of transitioning to a flowable state upon application of heat.

18. The device of claim 17, wherein the drive mechanism comprises a heat source for transitioning the substance to the flowable state, thereby causing the substance to flow through the reservoir to expel the fluid to be delivered to the user from the reservoir.

19. The self-injection device of claim 1, wherein the volume of the functional portion of the self-injection device comprises volumes of the substrate and elements connected thereto.

20. The self-injection device of claim 1, wherein the substrate comprises a glass chip.

21. The self-injection device of claim 1, wherein the non-functional portion of the interior volume of the housing comprises one or more aesthetic elements which are unrelated to drug delivery.

22. A self-injection device with miniaturized drug delivery components, the device comprising:
a housing having an interior volume, the interior volume consisting of a functional portion and a non-functional portion,
the functional portion comprising:
a substrate having a depression or cavity extending inwardly from a surface thereof, the depression or cavity defining a reservoir containing a single dose of a fluid to be delivered to a user;
a microneedle mounted to the substrate in fluid communication with the reservoir and extendable through the housing; and
a drive mechanism in communication with the substrate for expelling the fluid from the reservoir through the microneedle,
wherein an R value for the self-injection device defined by the equation $$R = \frac{L3_{Functional\_portion}}{L3_{housing}}$$

is less than 50%, and wherein $L3_{Functional\ Portion}$ is a longest length of the functional portion and $L3_{Housing}$ is a longest length of the interior volume of the housing.

23. The self-injection device of claim 22, wherein a dimension of the functional portion divided by a corresponding length of the housing is less than 40%.

24. A system for self-injection comprising:
a self-injection device having a housing having an interior volume consisting of a functional portion and a non-functional portion, the functional portion comprising:
a substrate having a depression or cavity extending inwardly from a surface thereof, the depression or cavity defining a reservoir containing a single dose of a fluid to be delivered to a user;
a microneedle mounted to the substrate in fluid communication with the reservoir and extendable through the housing; and
a drive mechanism in communication with the substrate for expelling the fluid from the reservoir through the microneedle; and
an external controller in communication with the drive mechanism deployable to initiate expulsion of the fluid from the reservoir through the microneedle,
wherein a volume of the functional portion of the interior volume is less than 40% of the interior volume of the housing.

25. The system of claim 24, wherein the drive mechanism of the self-injection device is activated by a signal sent from the external controller.

26. The system of claim 24, wherein the self-injection device sends a signal to the external controller when the expulsion of the fluid from the reservoir is substantially complete.

* * * * *